United States Patent [19]

Jones et al.

[11] 4,066,776
[45] Jan. 3, 1978

[54] ANTI-BACTERIAL COMPOSITIONS CONTAINING CERTAIN 3-NITROPYRAZOLES

[75] Inventors: Reuben G. Jones, Cedar City, Utah; Norman H. Terando, Indianapolis, Ind.

[73] Assignee: Eli Lilly and Company, Indianapolis, Ind.

[21] Appl. No.: 697,516

[22] Filed: June 18, 1976

Related U.S. Application Data

[63] Continuation-in-part of Ser. No. 561,139, March 24, 1975, abandoned, which is a continuation-in-part of Ser. No. 477,118, June 6, 1974, abandoned, which is a continuation-in-part of Ser. No. 357,135, May 4, 1973, abandoned, which is a continuation-in-part of Ser. No. 211,791, Dec. 23, 1971, abandoned, which is a continuation-in-part of Ser. No. 124,463, March 15, 1971, abandoned.

[51] Int. Cl.$^2$ .......................................... C07D 231/16
[52] U.S. Cl. ........................... 424/270; 260/294.8 R; 260/294.1; 260/295 H; 260/302 H; 260/306.8 D; 548/374; 548/377; 474/263; 474/273 P; 542/408
[58] Field of Search ....................... 424/273, 270, 263; 260/310 R

[56] References Cited

U.S. PATENT DOCUMENTS 3,121,092  2/1964  Geiszler ............................... 424/273

*Primary Examiner*—Richard J. Gallagher
*Attorney, Agent, or Firm*—William E. Maycock; Joseph A. Jones; Everet F. Smith

[57] ABSTRACT

Novel 1,4-disubstituted-3-nitropyrazoles having antimicrobial, parasiticidal, and herbicidal activity are prepared by a reaction sequence of which the individual steps are conventional. The new 3-nitropyrazoles are characterized by a 1-substituent and a usually carbonyl-containing 4-substituent. The novel 3(5)-nitro-4-pyrazole-carbonitrile is obtained as an intermediate in the preparation of the biologically-active compounds. Preferred compounds are 1-alkyl or -alkenyl-4-pyrazolecarboxamides and carbonitriles. The new compounds are particularly useful for the control of bacterial animal diseases.

30 Claims, No Drawings

ANTI-BACTERIAL COMPOSITIONS CONTAINING CERTAIN 3-NITROPYRAZOLES

CROSS-REFERENCE

This application is a continuation-in-part of our copending application Ser. No. 561,139, filed Mar. 24, 1975, now abandoned, which is a continuation-in-part of our then copending application Ser. No. 477,118, filed June 6, 1974, now abandoned, which was a continuation-in-part of our then copending application Ser. No. 357,135, filed May 4, 1973, now abandoned, which was a continuation-in-part of our then copending application Ser. No. 211,791, filed Dec. 23, 1971, now abandoned, which was a continuation-in-part of our then copending application Ser. No. 124,463, filed Mar. 15, 1971, now abandoned.

BACKGROUND OF THE INVENTION

One of the major goals of organic chemical research has always been the synthesis of antimicrobial compounds. Such compounds have been and continue to be in demand for use as human and veterinary medicines, as disinfectants for hospitals, floors and the like, and as agents for control of plant diseases. There is a continuing demand for antimicrobials cheaper and safer than those in use, as well as compounds for the control of organisms which have grown resistant to the compounds now in use.

A number of useful antimicrobials have come from the general field of hetero-ring compounds. The nitrofurans, for example, have yielded several valuable compounds. Many other ring systems have not been extensively explored as a source of antimicrobials. The 3-nitropyrazoles, for example, have appeared only occasionally in the chemical literature, and have not previously been known as microbiocides.

Habraken et al., Tetrahedron Letters 7, 479 (1970), disclosed the preparation of 1-methyl-3-nitro-4-pyrazolecarboxylic acid by nitration of a 1,4-dimethylpyrazole with acetyl nitrate, followed by oxidation of the 4-methyl substituent.

Parham and Aldre, J. Org. Chem. 25, 1259 (1960), prepared as 3(5)-nitropyrazole by replacement of the amine group in 3(5)-amino-4-phenylpyrazole through an intermediate diazonium salt. The amino compound was dissolved in fluoboric acid solution, chilled in an ice-salt bath, and stirred while a cold solution of sodium nitrite was added very slowly. The diazonium fluoborate precipitated, was filtered off and washed, and was then converted into 3(5)-nitro-4-phenylpyrazole by reaction with sodium nitrite in the presence of metallic copper.

A preparation of 3-nitro-1-phenylpyrazole was taught by Coburn, J. Heterocyclic Chem. 7, 455 (1970). The process was an oxidation of 3-amino-1-phenylpyrazole with an excess of anhydrous peroxytrifluoroacetic acid. No utility of the product was disclosed, and the process was not extended to other 3-nitropyrazoles.

Another preparation of a 3-nitropyrazole was described by Parham and Bleasdale, J. Am. Chem. Soc. 73, 4664 (1951). They made 3(5)-nitro-4-phenylpyrazole from 3-bromo-3-nitro-4-phenylpyrazoline by decomposition with sodium bicarbonate. Their purified product was recovered by chromatography.

Wolf and Flanigan, U.S. Pat. No. 3,303,200, taught the preparation of 1-(2-hydroxyalkyl)pyrazoles. They disclosed that any of some 14 groups, including nitro, could be substituted at the 3-, 4-, or 5-positions on the pyrazole ring, but they taught no preparative methods or utility of 3-nitropyrazoles.

None of the above references taught antimicrobial, parasiticidal, or herbicidal properties for the compounds which they disclosed.

Cheng, J. Heterocyclic Chem. 5, 195 (1968), described a preparation of 1-methyl-5-nitro-4-pyrazolecarboxylic acid, which is isomeric with our 1-methyl-3-nitro-4-pyrazolecarboxylic acid. Derivatives of the 5-nitro acid, however, do not exhibit biological activity comparable to that of the corresponding 3-nitro derivatives.

Antimicrobial compounds somewhat related to the 3-nitropyrazoles are known. For example, Hoff, U.S. Pat. No. 3,715,364, disclosed an interesting series of antiparasitic 5-nitroimidazoles. A 4-nitro-5-pyrazolecarbonitrile, said to be useful as a coccidiostat, was disclosed by Geiszler, U.S. Pat. No. 3,121,092.

Interesting 5-nitroimidazoles, useful for the control of blackhead disease, were disclosed by Asato et al., U.S. Pat. No. 3,565,892, by Vatre et al., U.S. Pat. No. 3,439,097, and by Henry, U.S. Pat. No. 3,378,552.

SUMMARY

We have now discovered a class of 3-nitropyrazoles, substituted in the 1-position with an alkyl, alkenyl, cycloalkenyl, alkynyl, cycloalkyl, cycloalkylalkyl or aryl group, and in the 4-position with any of several groups, preferably carboxamides. Our nitropyrazole compounds have antimicrobial, particularly antibacterial, parasiticidal, and herbicidal properties which make them useful in preventing and alleviating diseases of plants and animals, and in eliminating weeds. Antibacterial compositions useful in treating bacterial diseases of animals are presented.

DESCRIPTION OF THE PREFERRED EMBODIMENT

Our newly invented 3-nitropyrazoles are represented by the following generic formula:

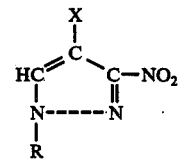

wherein R represents
A. $C_3$-$C_4$ epoxyalkyl,
B. hydrogen,
C. $C_1$-$C_{10}$ alkyl, $C_2$-$C_{10}$ alkenyl, $C_3$-$C_{10}$ alkynyl, $C_3$-$C_{10}$ cycloalkyl, cyclopropylmethyl, $C_3$-$C_{10}$ cycloalkenyl, $C_2$-$C_{10}$ alkyl mono- or disubstituted with halo or $C_1$-$C_3$ alkoxy, or $C_1$-$C_{10}$ alkyl mono- substituted with
  1. mercapto,
  2. carboxamido,
  3. keto oxygen,
  4. hydroxy,
  5. phthalimido,
  6. $C_1$-$C_3$ alkylthio,
  7. $C_1$-$C_3$ alkylsulfonyl,
  8. $C_1$-$C_3$ alkanoyl,
  9. phenyl,
  10. phenyl monosubstituted with
    a. $C_1$-$C_3$ alkyl, b. $C_1$-$C_3$ haloalkyl,
c. hydroxy, or
d. halo,

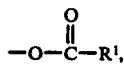 (11)

wherein $R^1$ represents
a. $C_1$-$C_3$ alkyl,
b. $C_1$-$C_3$ alkoxy,
c. $C_1$-$C_3$ haloalkyl,
d. amino,
e. $C_3$-$C_6$ cycloalkyl,
f. phenoxy,
g. phenyl, or
h. phenyl monosubstituted with
  1. $C_1$-$C_3$ alkyl,
  2. $C_1$-$C_3$ haloalkyl,
  3. halo, or
  4. hydroxy, or
12. cyano, or
D. phenyl, thiazolyl, or pyridyl, monosubstituted with nitro; and
X represents
A. thiadiazolyl,
B. thiadiazolyl monosubstituted with
  1. amino, or
  2. $C_1$-$C_2$ alkylamino,
C. cyano,

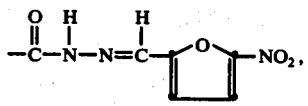 (D)

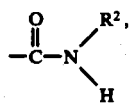 (E)

wherein $R^2$ represents
1. hydrogen, or
2. $C_1$-$C_6$ alkyl; or

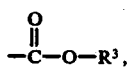 (F)

wherein $R^3$ represents $C_1$-$C_6$ alkyl; provided that a $C_1$ alkyl R group is substituted only with phenyl or substituted phenyl.

In the above generic formula, the various chemical groups bear their usual meanings in the organic chemical art. For the sake of complete clarity, examples of the various generally-named groups will be given.

The various alkyl, alkenyl, cycloalkyl, cycloalkenyl, alkynyl, and alkoxy groups which are named in the above description refer to substituents such as vinyl, 2-butenyl, 2,3-dimethyl-3-butenyl, 3-methylpentyl, cyclopropyl, cyclohexyl, cyclopentyl, methyl, t-butyl, 3-pentyl, 2-cyclobutenyl, cyclononyl, 3-cyclohexenyl, 4-cyclodecenyl, 2-decenyl, propargyl, 3-hexynyl, 9-decynyl, 2,4-hexadienyl, ethoxy, isopropoxy, hexyloxy, octyl, decyl, and 3-ethylhexyl.

Halo refers to fluoro, chloro, bromo, and iodo.

$C_1$-$C_3$ haloalkyl refers to substituents such as trifluoromethyl, 3-chloropropyl, and 2-bromoethyl.

$C_1$-$C_3$ alkylthio refers to substituents such as methylthio, ethylthio, and propylthio.

$C_1$-$C_3$ acyloxy refers to groups such as formyloxy, acetyloxy, and propionyloxy.

$C_1$-$C_3$ and $C_1$-$C_2$ alkylsulfonyl refer to substituents such as methylsulfonyl, ethylsulfonyl, and isopropylsulfonyl.

$C_1$-$C_3$ alkanoyl refers to substituents such as formyl, acetyl, and propionyl.

$C_1$-$C_2$ alkylamino refers to methylamino and ethylamino.

It will be understood that the present invention may be practiced in a number of different ways, making use of different types or classes of compounds. Various classes of compounds are also used in making use of the antibacterial compositions. For example, the following classes of compounds of the invention are contemplated, both as new compositions of matter and for use in the antibacterial compositions of this invention. Each numbered subparagraph below describes an independent class of compounds of the invention; in each class, the variable substituents have the general meanings above if not otherwise stated.

Compounds wherein:
1. R represents epoxyalkyl;
2. R represents hydrogen, alkyl, alkenyl, alkynyl, cyclopropylmethyl, cycloalkyl, cycloalkenyl, alkyl mono- or disubstituted with halo or alkoxy, or alkyl monosubstituted with mercapto, carboxamido, keto oxygen, hydroxy, phthalimido, alkylthio, alkylsulfonyl, alkanoyl, phenyl, substituted phenyl, cyano or

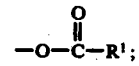

3. R represents phenyl, thiazolyl or pyridyl, monosubstituted with nitro;
4. R represent phenyl monosubstituted with nitro;
5. R represents thiazolyl or pyridyl, monosubstituted with nitro;
6. R represents hydrogen, alkyl, alkenyl, alkynyl, cyclopropylmethyl, cycloalkyl, cycloalkenyl, alkyl mono- or disubstituted with halo or alkoxy, or alkyl monosubstituted with mercapto, carboxamido, keto oxygen, hydroxy, alkylthio, alkylsulfonyl, alkanoyl, phenyl, substituted phenyl or cyano;
7. R represents hydrogen, alkyl, alkenyl, alkynyl, alkyl mono- or disubstituted with halo or alkoxy, or alkyl monosubstituted with mercapto, carboxamido, keto oxygen, hydroxy, alkylthio, alkylsulfonyl, alkanoyl, phenyl, substituted phenyl or cyano;
8. R represents hydrogen, alkyl, alkenyl, alkynyl, alkyl mono- or disubstituted with halo or alkoxy, or alkyl monosubstituted with mercapto, carboxamido, keto oxygen, hydroxy, alkylthio, alkylsulfonyl or alkanoyl;
9. R represents hydrogen, alkyl, alkenyl, cyclopropylmethyl, alkyl mono- or disubstituted with halo or alkoxy, or alkyl monosubstituted with hydroxy or alkylsulfonyl;
10. R represents hydrogen, $C_1$-$C_4$ alkyl, $C_2$-$C_3$ alkenyl, cyclopropylmethyl, $C_2$-$C_4$ alkyl mono- or disubstituted with halo or alkoxy, or $C_2$-$C_4$ alkyl monosubstituted with hydroxy or alkylsulfonyl;
11. R represents alkyl monosubstituted with phthalimido;
12. R represents alkyl monosubstituted with

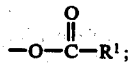

13. X represents thiadiazolyl or substituted thiadiazolyl;
14. X represents

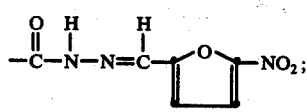

15. X represents cyano,

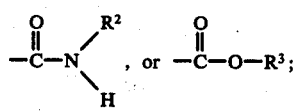

16. X represents cyano or

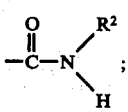

17. X represents

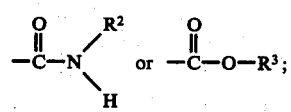

18. X represents cyano;
19. X represents

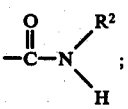

20. the compounds as described by subparagraphs 1 and 13;
21. the compounds as described by subparagraphs 1 and 14;
22. the compounds as described by subparagraphs 1 and 15;
23. the compounds as described by subparagraphs 1 and 16;
24. the compounds as described by subparagraphs 1 and 17;
25. the compounds as described by subparagraphs 1 and 18;
26. the compounds as described by subparagraphs 1 and 19;
27. the compounds as described by subparagraphs 2 and 13;
28. the compounds as described by subparagraphs 2 and 14;
29. the compounds as described by subparagraphs 2 and 15;
30. the compounds as described by subparagraphs 2 and 16;
31. the compounds as described by subparagraphs 2 and 17;
32. the compounds as described by subparagraphs 2 and 18;
33. the compounds as described by subparagraphs 2 and 19;
34. the compounds as described by subparagraphs 3 and 13;
35. the compounds as described by subparagraphs 3 and 14;
36. the compounds as described by subparagraphs 3 and 15;
37. the compounds as described by subparagraphs 3 and 16;
38. the compounds as described by subparagraphs 3 and 17;
39. the compounds as described by subparagraphs 3 and 18;
40. the compounds as described by subparagraphs 3 and 19;
41. the compounds as described by subparagraphs 4 and 13;
42. the compounds as described by subparagraphs 4 and 14;
43. the compounds as described by subparagraphs 4 and 15;
44. the compounds as described by subparagraphs 4 and 16;
45. the compounds as described by subparagraphs 4 and 17;
46. the compounds as described by subparagraphs 4 and 18;
47. the compounds as described by subparagraphs 4 and 19;
48. the compounds as described by subparagraphs 5 and 13;
49. the compounds as described by subparagraphs 5 and 14;
50. the compounds as described by subparagraphs 5 and 15;
51. the compounds as described by subparagraphs 5 and 16;
52. the compounds as described by subparagraphs 5 and 17;
53. the compounds as described by subparagraphs 5 and 18;
54. the compounds as described by subparagraphs 5 and 19;
55. the compounds as described by subparagraphs 6 and 13;
56. the compounds as described by subparagraphs 6 and 14;
57. the compounds as described by subparagraphs 6 and 15;
58. the compounds as described by subparagraphs 6 and 16;
59. the compounds as described by subparagraphs 6 and 17;
60. the compounds as described by subparagraphs 6 and 18;
61. the compounds as described by subparagraphs 6 and 19;
62. the compounds as described by subparagraphs 7 and 13;
63. the compounds as described by subparagraphs 7 and 14;
64. the compounds as described by subparagraphs 7 and 15;
65. the compounds as described by subparagraphs 7 and 16;

66. the compounds as described by subparagraphs 7 and 17;
67. the compounds as described by subparagraphs 7 and 18;
68. the compounds as described by subparagraphs 7 and 19;
69. the compounds as described by subparagraphs 8 and 13;
70. the compounds as described by subparagraphs 8 and 14;
71. the compounds as described by subparagraphs 8 and 15;
72. the compounds as described by subparagraphs 8 and 16;
73. the compounds as described by subparagraphs 8 and 17;
74. the compounds as described by subparagraphs 8 and 18;
75. the compounds as described by subparagraphs 8 and 19;
76. the compounds as described by subparagraphs 9 and 13;
77. the compounds as described by subparagraphs 9 and 14;
78. the compounds as described by subparagraphs 9 and 15;
79. the compounds as described by subparagraphs 9 and 16;
80. the compounds as described by subparagraphs 9 and 17;
81. the compounds as described by subparagraphs 9 and 18;
82. the compounds as described by subparagraphs 9 and 19;
83. the compounds as described by subparagraphs 10 and 13;
84. the compounds as described by subparagraphs 10 and 14;
85. the compounds as described by subparagraphs 10 and 15;
86. the compounds as described by subparagraphs 10 and 16;
87. the compounds as described by subparagraphs 10 and 17;
88. the compounds as described by subparagraphs 10 and 18;
89. the compounds as described by subparagraphs 10 and 19;
90. the compounds as described by subparagraphs 11 and 13;
91. the compounds as described by subparagraphs 11 and 14;
92. the compounds as described by subparagraphs 11 and 15;
93. the compounds as described by subparagraphs 11 and 16;
94. the compounds as described by subparagraphs 11 and 17;
95. the compounds as described by subparagraphs 11 and 18;
96. the compounds as described by subparagraphs 11 and 19;
97. the compounds as described by subparagraphs 12 and 13;
98. the compounds as described by subparagraphs 12 and 14;
99. the compounds as described by subparagraphs 12 and 15;
100. the compounds as described by subparagraphs 12 and 16;
101. the compounds as described by subparagraphs 12 and 17;
102. the compounds as described by subparagraphs 12 and 18;
103. the compounds as described by subparagraphs 12 and 19.

The characterizing feature of our invention is the 3-nitropyrazole nucleus. As would be expected, our 3-nitropyrazoles of different substitution patterns all have basically similar antimicrobial activity. It is surprising that the great biological activity of our compounds is limited to the 3-nitropyrazoles which we have disclose.

It would be expected that joining two or more 3-nitropyrazole nuclei would produce biologically-active compounds, in view of the activity of the single-ring compounds. We have shown that compounds consisting of two or more 3-nitropyrazole units, linked through their 1- or 4-substituents, are active. A typical example of such a compound is 1,1'-(2,5-cyclohexadien-1,4-ylene)-bis(3-nitro-4-pyrazolecarboxamide),

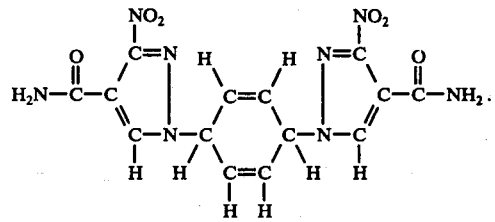

The following list of compounds exemplary of our invention is given in the interest of further clarity. Those skilled in the art will be able, by the study of these compounds, to recognize the broad scope of our invention which these named compounds illustrate. It is to be understood that our invention is not confined to the compounds listed.

1. 1-ethyl-3-nitro-4-pyrazolecarbonitrile
2. 2-(1-methyl-3-nitro-4-pyrazolyl)-5-methylamino-1,3,4-thiadiazole
3. 1-methyl-3-nitro-4-pyrazolecarboxamide
4. 1-propargyl-3-nitro-4-pyrazolecarbonitrile
5. 3-nitro-1-(4-nitrophenyl)-4-pyrazolecarboxamide
6. N-hexyl-1-(5-nitro-2-thiazolyl)-3-nitro-4-pyrazolecarboxamide
7. 1-(3-nitro-2-pyridyl)-3-nitro-4-pyrazolecarbonitrile
8. 1-(2-mercaptoethyl)-3-nitro-4-pyrazolecarboxamide
9. 1-(2-oxopropyl)-3-nitro-4-pyrazolecarboxamide
10. 1-(2-phthalimidoethyl)-3-nitro-4-pyrazolecarboxamide
11. 1-[2-(3-ethylphenyl)ethyl]-3-nitro-4-pyrazolecarboxamide 12. 1-[2-(2-trifluoromethylphenyl)ethyl]-3-nitro-4-pyrazolecarboxamide
13. 1-[2-(4-hydroxyphenyl)ethyl]-3-nitro-4-pyrazolecarboxamide
14. 1-[2-(4-bromophenyl)ethyl]-3-nitro-4-pyrazolecarboxamide
15. 1-[2-(2-chloropropionyloxy)ethyl]-3-nitro-4-pyrazolecarboxamide
16. 1-allyl-3-nitro-4-pyrazolecarboxamide
17. 1-phenethyl-3-nitro-4-pyrazolecarboxamide
18. 1-benzyl-3-nitro-4-pyrazolecarboxamide
19. 1-[2-(4-ethylbenzoyloxy)ethyl]-3-nitro-4-pyrazolecarboxamide
20. 1-(2-benzoyloxyethyl)-3-nitro-4-pyrazolecarboxamide
21. 1-[2-dichloromethylbenzoyloxy)ethyl]-3-nitro-4-pyrazolecarboxamide
22. 1-[2-(3-bromobenzoyloxy)ethyl]-3-nitro-4-pyrazolecarboxamide
23. 1-[2-(4-hydroxybenzoyloxy)ethyl]-3-nitro-4-pyrazolecarboxamide
24. 1-(2-hydroxybutyl)-3-nitro-4-pyrazolecarboxamide
25. 1-(3-hexyl)-3-nitro-4-pyrazolecarboxamide
26. butyl 1-(2-cyclopropenyl)-3-nitro-4-pyrazolecarboxylate
27. 1-(2,5-cyclohexadienyl)-3-nitro-4-pyrazolecarboxamide
28. 1-(4-chlorobenzyl)-3-nitro-4-pyrazolecarbonitrile
29. 1-(2,5-cyclodecadienyl)-3-nitro-4-pyrazolecarbonitrile
30. 1-methyl-3-nitro-4-pyrazolecarbonitrile
31. 1-(2,3-epoxypropyl)-3-nitro-4-pyrazolecarbonitrile
32. 1-(2-hydroxyethyl)-3-nitro-4-pyrazolecarboxamide
33. 1-(2-chloroethyl)-3-nitro-4-pyrazolecarbonitrile
34. 1-(2-ethoxyethyl)-3-nitro-4-pyrazolecarboxamide
35. 1-(2-ethylsulfonylethyl)-3-nitro-4-pyrazolecarboxamide
36. 1-(2-ethoxyethyl)-N-methyl-3-nitro-4-pyrazolecarboxamide
37. ethyl 3(5)-nitro-4-pyrazolecarboxylate
38. 3-notro-1-propyl-4-pyrazolecarboxamide
39. 1-(2-ethylsulfonylethyl)-N-methyl-3-nitro-4-pyrazolecarboxamide
40. N-methyl-3-nitro-1-(t-butyl)-4-pyrazolecarboxamide
41. 1-(2-fluoroethyl)-3-nitro-4-pyrazolecarbonitrile
42. 1-(3-hexyl)-3-nitro-4-pyrazolecarbonitrile
43. 1-(3-methyl-2-pentyl)-3-nitro-4-pyrazolecarboxamide
44. 1-(4-hydroxybutyl)-N-methyl-3-nitro-4-pyrazolecarboxamide
45. 1-cyclopropylmethyl-N-ethyl-3-nitro-4-pyrazolecarboxamide
46. N-butyl-1-(2-butenyl)-3-nitro-4-pyrazolecarboxamide
47. 1-(3-hydroxy-2-pentyl)-3-nitro-N-pentyl-4-pyrazolecarboxamide
48. 3-nitro-1-nonyl-4-pyrazolecarboxamide
49. methyl 1-methyl-3-nitro-4-pyrazolecarboxylate
50. t-butyl 1-(3,3-difluoropropyl)-3-nitro-4-pyrazolecarboxylate
51. 1-(2-acetylethyl)-3-nitro-4-pyrazolecarbonitrile
52. 1-(2-chloroethyl)-3-nitro-4-pyrazolecarboxamide
53. 1-(2-chloroethyl)-N-methyl-3-nitro-4-pyrazolecarboxamide
54. 3(5)-nitro-4-pyrazolecarbonitrile
55. 1-(2-hydroxyethyl)-3-nitro-4-pyrazolecarbonitrile
56. 1-(3,4-epoxybutyl)-N-methyl-3-nitro-4-pyrazolecarboxamide
57. 1-(2,3-epoxyporpyl)-3-nitro-4-pyrazolecarboxamide
58. 1-(2-hydroxyethyl)-N-methyl-3-nitro-4-pyrazolecarboxamide
59. 1,1'-(2,5-cyclohexadien-1,4-ylene)-bis(3-nitro-4-pyrazolecarboxamide)
60. 3(5)-nitro-4-pyrazolecarboxamide
61. N,1-dimethyl-3-nitro-4-pyrazolecarboxamide
62. 1-(3-hydroxypropyl)-3-nitro-4-pyrazolecarboxamide
63. 1-(3-chloropropyl)-3-nitro-4-pyrazolecarboxamide
64. 1-isopropyl-3-nitro-4-pyrazolecarboxamide
65. 1-(2-methoxyethyl)-3-nitro-4-pyrazolecarboxamide
66. 1-[2-(methylsulfonyl)ethyl]-3-nitro-4-pyrazolecarboxamide
67. 1-(2,2-diethoxyethyl)-3-nitro-4-pyrazolecarbonitrile
68. 3-nitro-1-(5-nitro-2-thiazolyl)-4-pyrazolecarbonitrile
69. 1-(2-hydroxypropyl)-3-nitro-4-pyrazolecarboxamide
70. 1-benzyl-3-nitro-4-pyrazolecarbonitrile
71. methyl 1-(2-hydroxyethyl)-3-nitro-4-pyrazolecarboxylate
72. 1-(2-ethylthioethyl)-3-nitro-4-pyrazolecarbonitrile
73. 4-cyano-3-nitro-1-pyrazolepropionitrile
74. 1-methyl-3-nitro-4-pyrazolecarboxylic acid, 5-nitrofurfurylidene hydrazide
75. 1-(2-butenyl)-3-nitro-4-pyrazolecarboxamide
76. [2-(4-carbamoyl-3-nitropyrazol-1-yl)ethyl] p-toluate
77. [2-(4-carbamoyl-3-nitropyrazol-1-yl)ethyl] phenyl carbonate
78. [2-(4-carbamoyl-3-nitropyrazol-1-yl)ethyl] ethyl carbonate
79. 4-carbamoyl-3-nitro-1-pyrazolepropionamide
80. 2-(4-carbamoyl-3-nitropyrazol-1-yl)ethyl acetate
81. 3-nitro-1-vinyl-4-pyrazolecarboxamide
82. 1-(2,2-diethoxyethyl)-3-nitro-4-pyrazolecarboxamide
83. 1-(3-chloropropyl)-3-nitro-4-pyrazolecarbonitrile
84. 1-(2-ethoxyethyl)-3-nitro-4-pyrazolecarbonitrile
85. N-butyl-1-(2-hydroxyethyl)-3-nitro-4-pyrazolecarboxamide
86. 1-(2-ethylsulfonylethyl)-3-nitro-4-pyrazolecarbonitrile
87. 1-cyclopropylmethyl-3-nitro-4-pyrazolecarbonitrile
88. 1-(2-hydroxyethyl)-N-isopropyl-3-nitro-4-pyrazolecarboxamide
89. 3-nitro-1-nonyl-4-pyrazolecarbonitrile
90. 1-cyclopropylmethyl-3-nitro-4-pyrazolecarboxamide
91. 1-(2-bromoethyl)-3-nitro-4-pyrazolecarbonitrile
92. 3-nitro-1-(4-nitrophenyl)-4-pyrazolecarbonitrile
93. [2-(4-carbamoyl-3-nitropyrazol-1-yl)ethyl] carbamate
94. 1-(2-hydroxyethyl)-3-nitropyrazole-4-carboxylic acid, 5-nitrofurfurylidene hydrazide
95. 3-nitro-1-(5-nitro-2-thiazolyl)pyrazole-4-carboxamide
96. 1-(2-bromoethyl)-3-nitropyrazole-4-carboxamide
97. 1-[2-(methylthio)ethyl]-3-nitropyrazole-4-carboxamide
98. 2-(4-carbamoyl-3-nitropyrazol-1-yl)ethyl 3,4-dichlorobenzoate
99. 2-(4-carbamoyl-3-nitropyrazol-1-yl)ethyl m-chlorobenzoate
100. 1-allyl-3-nitropyrazole-4-carbonitrile
101. N-[2-(4-cyano-3-nitropyrazol-1-yl)ethyl] phthalimide 102. 2-amino-5-(1-methyl-3-nitro-4-pyrazolyl)-1,3,4-thiadiazole A preferred intermediate in the preparation of other compounds of our invention is 3(5)-nitro-4-pyrazolecarbonitrile. The importance of substituted 4-pyrazolecarbonitriles as intermediates is illustrated below and in the examples. The specific nitrile is of particular importance because it bears no 1-substituent and therefore can be 1-substituted as the chemist desires.

All of our pyrazole compounds are prepared from 3(5)-amino-4-pyrazolecarbonitrile. The nitrile can be purchased commercially. The substituents at the 1- and 4-positions are individually attached to the pyrazole molecule in separate steps, after conversion of the amino function to nitro.

Skilled organic chemists will recognize that the described synthetic methods are not the only ways to prepare our compounds. Our methods are effective and proven, but other reactions, performed in other orders, can be used to prepare our 3-nitropyrazoles.

The first step in our preferred synthesis is the conversion of the amine function in 3(5)-amino-4-pyrazolecarbonitrile to a nitro function. The conversion is accomplished in two stages by forming the diazonium fluoborate salt, and then replacing the diazonium group by the nitro group with $NaNO_2$ in the presence of copper. Reaction conditions and purification methods are described below which produce a yield of 79 percent from the two-stage reaction.

The 1-alkyl, -alkenyl, -cycloalkyl, -cycloalkylalkyl, -cycloalkenyl, -alkynyl, or -aryl substituent is then attached to the pyrazole ring. A 1-sodium salt is first made, with NaH for example. The salt is reacted with a halo derivative of the desired 1-substituent, eliminating sodium halide and producing the desired substitution.

The reaction sequence is complete at this point, if the desired compound is a 3-nitro-1-substituted-4-pyrazolecarbonitrile. Such compounds are useful antimicrobials, parasiticides and herbicides. If a 4-substituent other than cyano is desired, conversion of the cyano group is necessary as the third stage of synthesis.

A 4-carboxylic acid derivative is made by hydrolysis with acid or with an alkali hydroxide. The carboxylic acid substituent is converted to the carboxamide through a carbonyl chloride derivative, or directly to carboxylates. The carboxylates can be converted to substituted carboxamides by direct reaction with the corresponding amines, or to hydrazides.

Other reaction sequences can be effectively used. For example, 3(5)-nitro-4-pyrazolecarbonitrile may be hydrolyzed to 3(5)-nitro-4-pyrazolecarboxylic acid, to which one of our 1-substituents may be attached at the 1-position as explained above and in the examples below.

The following examples show in detail the reaction conditions which are used to produce our compounds. The compounds which were products of the reactions reported below were identified by nuclear magnetic resonance analysis and in some cases by infrared analysis.

EXAMPLE 1

3(5)-nitro-4-pyrazolecarbonitrile

A suspension was made of 64.8 gm. of 3(5)-amino-4-pyrazolecarbonitrile in 300 ml. of 48% $HBF_4$ at room temperature. The suspension was cooled to $-5°$ C., with stirring, and a cold solution of 42 gm. of $NaNO_2$ in 84 ml. of water was added dropwise over a one-hour period while the temperature of the mixture was held at approximately $-5°$ to $0°$ C. The mixture was stirred at $-5°$ C. for one-half hour after completion of the addition, and the diazonium fluoborate salt was filtered off and washed, first with 125 ml. of cold ethanol and then several times with anhydrous ether, and dried over $P_2O_5$ under vacuum. The yield was 124 gm. of the 3(5)-diazonium fluoborate salt of 4-pyrazolecarbonitrile, m.p. 104° C. dec.

The salt obtained above was added in portions over a period of two hours to a stirred mixture of 300 gm. of $NaNO_2$, 500 ml. of water, and 25 gm. of finely-divided copper at 20°-25° C. After completion of the addition, the mixture was stirred an additional 2 hours at 25° C., then cooled to 0° C. and filtered. The filter cake was pressed as dry as possible and washed with 200 ml. of ice water. The washed solid was suspended in 300 ml. of water, cooled in an ice bath, and 60 ml. of 6N HCl was added with stirring.

To this mixture was then added one liter of ethyl acetate, and after thorough mixing, the emulsion was filtered through a layer of filter aid. The organic layer was separated, dried over $MgSO_4$, and evaporated to dryness. The residue was decolorized and recrystallized from methanol water to yield, after drying, 67.5 gm. of 3(5)-nitro-4-pyrazolecarbonitrile, m.p. 154°-156° C.

EXAMPLE 2

1-(2-hydroxyethyl)-3-nitro-4-pyrazolecarbonitrile

A solution was made of 32 gm. of 3(5)-nitro-4-pyrazolecarbonitrile in 25 ml. of 1,2-dimethoxyethane. The solution was added dropwise to a stirred suspension of 2.4 gm. of NaH in 25 ml. of 1,2-dimethoxyethane under nitrogen. After the evolution of hydrogen had ceased, the product was separated by filtration. After drying under vacuum at 120° C., there was obtained 36 gm. of 3(5)-nitro-4-pyrazolecarbonitrile sodium salt, m.p. 260°-262° C. dec.

A solution was made of 32 gm. of the above product in 200 ml. of acetonitrile and 25 gm. of 2-bromoethanol. The mixture was stirred at 55°-60° C. for 15 hours. The reaction mixture was cooled to room temperature, poured into cold water, and extracted with ethyl acetate. The organic layer was washed with cold, saturated NaCl solution, dried over $MgSO_4$, and evaporated under vacuum. The residue was an oil which crystallized upon cooling and scratching. The crystals were recrystallized from methanol-water to yield 20 gm. of 1-(2-hydroxyethyl)-3-nitro-4-pyrazolecarbonitrile, m.p. 79°-81° C.

The alkyl, alkenyl, alkynyl, cycloalkyl, cycloalkylalkyl, and cycloalkenyl substituents at the 1-position of the pyrazole molecule are added by the above typical procedure. The reactants are compounds which consist of the desired 1-substituent moiety with a halogen atom, or other suitable substituent such as tosyl, at the desired point of attachment to the 1-position of the pyrazole molecule. Minor changes in the reaction conditions will, of course, be required; but these variations can readily be supplied by those skilled in the art. Listed below are typical, but not exhaustive, examples of our 1-substituents and the reactant compounds from which they are prepared.

| Reactant | 1-Substituent |
|---|---|
| 1-bromo-2-chloroethane | 2-chloroethyl |

| Reactant | 1-Substituent |
|---|---|
| bromocyclohexane | cyclohexyl |
| bromocyclopropylmethane | cyclopropylmethyl |
| 1-chloro-2-ethylsulfonyl-ethane | 2-ethylsulfonyl ethyl |
| 1-bromo-5-methylmercapto-octane | 5-methylmercapto-octyl |
| 1-bromo-2-ethylthio-propane | 2-ethylthiopropyl |
| 1-chloro-3-acetylhexane | 3-acetylhexyl |
| 1-chloro-propionamide | propionamido |
| 1-bromo-3-chloro-2-2-pentene | 3-chloro-2-pentenyl |
| ethyl iodide | ethyl |
| benzyl chloride | benzyl |

An alternate procedure for preparing 1-substituted pyrazoles is illutrated in the following example of the preparation of 1-methyl-3-nitro-4-pyrazolecarbonitrile.

EXAMPLE 3

1-methyl-3-nitro-4-pyrazolecarbonitrile

Twenty gm. of 3(5)-nitro-4-pyrazolecarbonitrile was dissolved in 150 ml. of 1,2-dimethoxyethane, and 54 gm. of methyl iodide and 21.4 gm. of anhydrous $K_2CO_3$ were added. The stirred mixture was refluxed for 15 hours. The mixture was then cooled and filtered, and the solids were washed with 1,2-dimethoxyethane. Evaporation of the filtrate and wash liquor under vacuum yielded an oil. The oil was dissolved in ethyl acetate and washed successively with $K_2CO_3$ solution, saturated $Na_2S_2O_3$ solution, and water. After drying over $MgSO_4$ the solvent was removed under vacuum yielding a solid. Recrystallizing the solid from benzene produced 18.7 gm. of 1-methyl-3-nitro-4-pyrazolecarbonitrile, m.p. 85°–87° C.

The following group of examples show the attachment of a variety of 1-substituents on our 3-nitropyrazoles.

EXAMPLE 4

1-(2,3-epoxypropyl)-3-nitro-4-pyrazolecarbonitrile

A mixture of 2.76 gm. of 3(5)-nitro-4-pyrazolecarbonitrile, 14 ml. of epichlorohydrin and 230 mg. of anhydrous $K_2CO_3$ was heated to reflux with stirring for 10 minutes. The hot mixture was then filtered and the inorganic solid material was washed with hot ethanol. The filtrate plus the wash liquor was evaporated under vacuum to isolate 1-(2-hydroxy-3-chloropropyl)-3-nitro-4-pyrazolecarbonitrile as an orange oil. The oil was dissolved in 100 ml. of ethyl acetate, 10 ml. of 10% of NaOH was added, and the mixture was stirred for 30 minutes. The organic layer was separated, washed with cold water, and dried over $MgSO_4$. Evaporation under vacuum yielded an oil which crystallized upon cooling. Decolorization and recrystallization of the crude solid from ethyl acetate-benzene yielded 2 gm. of 1-(2,3-epoxypropyl)-3-nitro-4-pyrazolecarbonitrile, m.p. 78°–80° C.

EXAMPLE 5

1-(4-nitrophenyl)-3-nitro-4-pyrazolecarbonitrile

A solution was made of 8 gm. of 3(5)-nitro-4-pyrazolecarbonitrile sodium salt (made in Example 2 above) in 40 ml. of anhydrous DMF, 8.4 gm. of 4-fluoronitrobenzene was added, and the mixture was heated to 120°–125° C. for 5 hours with stirring. The mixture was then cooled to room temperature and poured into 150 ml. of cold water. The two-phase mixture was extracted with ethyl acetate, and the organic layer was washed with cold salt-water and dried over magnesium sulfate. Evaporation of the solvent yielded 10 gm. of 1-(4-nitrophenyl)-3-nitro-4-pyrazolecarbonitrile, m.p. 172°–175° C.

The following aryl substituents and the reactants from which they are produced are exemplary of our 1-aryl substituents.

| Reactant | Substituent |
|---|---|
| 2-bromo-4-nitrothiazole | 4-nitro-2-thiazolyl |
| 3-bromo-4-nitropyridine | 4-nitro-3-pyridyl |

Our compounds containing an acyloxy substituent on the 1-substituent are made by a multiple-step procedure. A 1-substituent, having a hydroxy group where the acyl group is to be, is added to the nucleus, and then a reaction of the following type is carried out.

EXAMPLE 6

2-(4-carbamoyl-3-nitropyrazol-1-yl)ethyl acetate

A 5 gm. portion of 1-(2-hydroxyethyl)-3-nitro-4-pyrazolecarboxamide was suspended in 25 ml. of acetic anhydride at room temperature, and 5 drops of pyridine were added. The mixture was heated on a steam bath for 1 hour, cooled to room temperature, and poured into 150 ml. of cold water. A white solid precipitated which was recovered by filtration, washed with water, and dried. Recrystallization of the solid from methanol produced 4 gm. of 2-(4-carbamoyl-3-nitropyrazol-1-yl)ethyl acetate, m.p. 139°–41° C.

The following three examples illustrate further syntheses of our compounds having other 1-substituents.

EXAMPLE 7

[2-(4-carbamoyl-3-nitropyrazol-1-yl)ethyl] phenyl carbonate

A 20 gm. portion of 1-(2-hydroxyethyl)-3-nitro-4-pyrazolecarboxamide was dissolved in 150 ml. of pyridine and the solution was cooled with stirring to 15°–20° C. Sixteen gm. of phenylchloroformate was added dropwise to the cool mixture over a period of 10–15 minutes while holding the temperature constant. After the addition was complete, the reaction was heated to 55°–60° C. and stirred for 1 hour. The reaction mixture was then cooled to room temperature, poured into 1 liter of water with stirring, and the mixture was chilled in an ice bath. A white solid precipitated and was filtered off. The filtered solids were washed thoroughly with cold water, dissolved in methanol, and decolorized with activated carbon. Recrystallization of the product from methanol yielded 12 gm. of [2-(4-carbamoyl-3-nitropyrazol-1yl)ethyl] phenyl carbonate, m.p. 108°–110° C.

EXAMPLE 8

[2-(4-carbamoyl-3-nitropyrazol-1-yl)ethyl] carbamate

Eight gm. of [2-(4-carbamoyl-3-nitropyrazol-1-yl)ethyl] phenyl carbonate was suspended in 150 ml. of methanol at ice bath temperature. The mixture was saturated, with stirring, with ammonia over a period of 1–2 hours. The starting compound dissolved. The solution was allowed to warm to room temperature and to stand overnight, during which time a solid precipitated. The reaction mixture was evaporated to dryness under vacuum, water was added to the residue, and the solids were filtered off. The filtered solids were thoroughly washed with cold water, and dried under vacuum. Recrystallization from methanol-dimethylformamide produced 1.2 gm. of [2-(4-carbamoyl-3-nitropyrazol-1-yl)ethyl] carbamate, m.p. 191°–194° C.

EXAMPLE 9

4-cyano-3-nitro-1-pyrazolepropionitrile

A 13.8 gm. portion of 3(5)-nitro-4-pyrazolecarbonitrile was dissolved in 150 ml. of absolute ethanol. To the solution was added in order 5.3 gm. of anhydrous sodium carbonate and 13.4 gm. of 3-bromopropionitrile. The reaction mixture was stirred under reflux for 10 hours, and the solvent was then removed under vacuum. Water was added to the white solid residue and the aqueous mixture was extracted with ethyl acetate. The organic layer was then washed with salt water and dried over magnesium sulfate. Evaporation of the solvent under vacuum and recrystallization of the solid from ethyl acetate-methanol produced 8 gm. of 4-cyano-3-nitro-1-pyrazolepropionitrile, m.p. 137°–139° C.

The following two examples complete the description of the 1-substituent reactions which form our compounds. There is no need to exemplify the synthesis of all compounds of our invention, since those skilled in the art can readily design all the syntheses from our teaching combined with their skill.

EXAMPLE 10

1-(2-bromoethyl)-3-nitro-4-pyrazolecarboxamide

A suspension was made of 10 gm. of 1-(2-hydroxyethyl)-3-nitro-4-pyrazolecarboxamide in 150 ml. of 1,2-dimethoxyethane. While stirring, 14 gm. of $PBr_3$ was added dropwise over a 1-hour period. After the addition, the mixture was stirred at 45°–50° C. for 10 hours. Then the solvent was removed under vacuum, and the residue taken up in ethyl acetate. The organic layer was washed with aqueous $NaHCO_3$, washed with brine, and dried over anhydrous $MgSO_4$. Evaporation of the solvent under vacuum produced a white solid, which was recrystallized from methanol to produce 6 gm. of 1-(2-bromoethyl)-3-nitro-4-pyrazolecarboxamide, m.p. 135°–37° C.

EXAMPLE 11

3-nitro-1-vinyl-4-pyrazolecarboxamide

A suspension of 5 gm. of 1-(2-bromoethyl)-3-nitro-4-pyrazolecarboxamide in 100 ml. of 5 percent $Na_2CO_3$ solution was refluxed with stirring for 5 hours. The mixture was cooled in an ice bath and acidified to pH 2 with concentrated HCl. The product precipitated and was separated by filtration. The solids were washed with cold water and recrystallized from methanol-water to produce 2 gm. of 3-nitro-1-vinyl-4-pyrazolecarboxamide, m.p. 150°–52° C.

Other 1-alkenyl-substituted compounds are made by analogous reactions.

| Reactant 1-substituent | Product 1-substituent |
|---|---|
| 3-bromopropyl | allyl |
| 4-bromobutyl | crotyl |

The following series of examples illustrate the reactions by which the 4-nitrile group of our starting compound is converted to other 4-substituents.

EXAMPLE 12

1-methyl-3-nitro-4-pyrazolecarboxylic acid

A solution was made of 350 ml. of water, 35 gm. of NaOH, and 32 gm. of 1-methyl-3-nitro-4-pyrazolecarbonitrile. The solution was refluxed for 18 hours, cooled in an ice bath, and then acidified to pH 2 with concentrated HCl. A solid precipitated, which was filtered, washed with cold water, and recrystallized from methanol-water. The yield was 32.5 gm. of 1-methyl-3-nitro-4-pyrazolecarboxylic acid, m.p. 185°–187° C.

EXAMPLE 13

1-(2-hydroxyethyl)-3-nitro-4-pyrazolecarboxylic acid

Fifteen gm. of 1-(2-hydroxyethyl)-3-nitro-4-pyrazolecarbonitrile was added to 150 ml. of concentrated HCl and stirred at 70°–75° C. for 10 hours. The resulting solution was evaporated to dryness under vacuum. The solid residue was suspended in 200 ml. of isopropanol, heated to boiling, cooled in an ice bath, and filtered to remove $NH_4Cl$. The residue left after evaporation of the filtrate under vacuum was an oil which crystallized upon cooling. Recrystallization of the crude crystals from benzene-ethyl acetate yielded 13.4 gm. of 1-(2-hydroxyethyl)-3-nitro-4-pyrazolecarboxylic acid, m.p. 147°–149° C.

The most valuable antimicrobial compounds of our invention are the 4-carboxamido compounds. The various carboxamides are made by procedures shown below.

EXAMPLE 14

1-methyl-3-nitro-4-pyrazolecarbonyl chloride

Twenty gm. of 1-methyl-3-nitro-4-pyrazolecarboxylic acid was suspended in 250 ml. of $CHCl_3$, 65 gm. of thionyl chloride was added, and the mixture was refluxed for three hours. The residue left after evaporation under vacuum was an oil which crystallized upon cooling. The crude product was triturated with petroleum ether-ethyl ether to yield 22.5 gm. of 1-methyl-3-nitro-4-pyrazolecarbonyl chloride, m.p. 68°–70° C.

EXAMPLE 15

1-methyl-3-nitro-4-pyrazolecarboxamide

Seven gm. of 1-methyl-3-nitro-4-pyrazolecarbonyl chloride was added in portions to 50 ml. of concentrated $NH_4OH$. The mixture was heated at reflux for 15 to 20 minutes, evaporated to dryness, and cooled. The resultant crystallized product was identified as 1-methyl-3-nitro-4-pyrazolecarboxamide, m.p. 190°–192° C.

EXAMPLE 16

N,1-dimethyl-3-nitro-4-pyrazolecarboxamide

Fifty ml. of water was cooled in an ice bath and saturated with monomethylamine. To the solution was added 2 gm. of 1-methyl-3-nitro-4-pyrazolecarbonyl chloride in portions, and the mixture was heated until the solid dissolved. Upon cooling a solid precipitated which was recrystallized from water and identified as 1.3 gm. of N,1-dimethyl-3-nitro-4-pyrazolecarboxamide, m.p. 163°–165° C.

The same reaction is used to produce other 4-carboxamide substituents within the scope of our invention.

The following substituents and their reactants are exemplary.

| Reactant | Substituent |
|---|---|
| hexylamine | hexylcarboxamide |
| 3-pentylamine | 3-pentylcarboxamide |
| ethylamine | ethylcarboxamide |

Our 4-carboxamides can also be made in one step directly from the corresponding 4-carbonitriles. The example below illustrates the process.

EXAMPLE 17

1-(2-hydroxyethyl)-3-nitro-4pyrazolecarboxamide

A 25 gm. portion of 1-(2-hydroxyethyl)-3-nitro-4-pyrazolecarbonitrile was dissolved in 200 ml. of methanol, and 110 ml. of 15 percent $H_2O_2$ was added. Then 8.5 ml. of 6N NaOH was added with stirring in small portions over a 30-minute period. The reaction mixture was externally cooled to keep its temperature below 50° C. The mixture was stirrred for 1 hour at 45°–50° C. after the addition was completed. Then the mixture was cooled to room temperature, the pH was adjusted to 8 by addition of concentrated HCl, and the solvent was removed under vacuum. The product crystallized during the evaporation, and was separated by filtration. Then the product was washed with cold water, dissolved in methanol, decolorized with charcoal, and recrystallized to produce 20 gm. of 1-(2-hydroxyethyl)-3-nitro-4-pyrazolecarboxamide, m.p. 148°–50° C.

The 4-esters have useful biological activity, and are also useful intermediates. The following example illustrates the synthesis of our 4-esters.

EXAMPLE 18 methyl 1-(2-hydroxyethyl)-3-nitro-4-pyrazolecarboxylate

Thirteen gm. of 1-(2-hydroxyethyl)-3-nitro-4-pyrazolecarboxylic acid was dissolved in 200 ml. of tetrahydrofuran and the solution was cooled in an ice bath. To the cold solution was added dropwise a slight excess of ethereal diazomethane. After the evolution of nitrogen had ceased, the solvents were removed under vacuum yielding an oil which crystallized upon cooling. Recrystallization of the crude solid from ether-acetone yielded 12 gm. of methyl 1-(2-hydroxyethyl)-3-nitro-4-pyrazolecarboxylate, m.p. 93°–95° C.

The example below illustrates another method of esterification which can be used to produce our 4-pyrazolecarboxylates.

EXAMPLE 19 methyl 1-(2-hydroxyethyl)-3-nitro-4-pyrazolecarboxylate

A methanol solution was made of 21.6 gm. of 1-(2-hydroxyethyl)-b 3-nitro-4-pyrazolecarboxylic acid. The solution was saturated with HCl, allowed to stand at room temperature for several hours, and evaporated. The residue was dissolved in ether, washed with $Na_2CO_3$ solution, and the ether layer was evaporated to dryness to yield 18 gm. of methyl 1-(2-hydroxyethyl)-3-nitro-4-pyrazolecarboxylate, m.p. 93°–95° C.

Other 4-esters are conveniently made by analogous reactions.

| Reactant | Substituent |
|---|---|
| ethanol | ethyl carboxylate |
| butanol | butyl carboxylate |
| hexanol | hexyl carboxylate |

The example below shows the synthesis of 4-pyrazolecarboxamides from 4-carboxylates.

EXAMPLE 20

1-(2-hydroxyethyl)-N-methyl-3-nitro-4-pyrazolecarboxamide

Four gm. of methyl 1-(2-hydroxyethyl)-3-nitro-4-pyrazolecarboxylate was dissolved in a cold mixture of 25 ml. of absolute methanol and 25 ml. of condensed monomethylamine. The solution was allowed to stand in a stoppered container for 48 hours at room temperature. Evaporation of the volatile liquids under vacuum yielded a solid, which after decolorization and recrystallization from methanolisopropanol was provided to be 2.3 gm. of 1-(2-hydroxyethyl)-N-methyl-3-nitro-4-pyrazolecarboxamide, m.p. 138°–140° C.

The following 4-amido substituents are typical of those which are prepared by the above reaction.

| Reactant | Substituent |
|---|---|
| n-butylamine | n-butylcarboxamide |
| isopropylamine | isopropylcarboxamide |

The following example illustrates syntheses of 4-pyrazole acid hydrazides which have important antimicrobial properties.

EXAMPLE 21

1-methyl-3-nitro-4-pyrazolecarboxylic acid, 5-nitrofurfurylidene hydrazide

A 5.55 gm. portion of 1-methyl-3-nitro-4-pyrazolecarboxylic acid, hydrazide was dissolved in aqueous ethanol at room temperature. To the solution was added a solution of 4.23 gm. of 5-nitrofurfuraldehyde in 50 ml. of ethanol. The reaction mixture was stirred for 10 minutes, and the product precipitated as a yellow solid. The mixture was stirred overnight, after which the solid was filtered away from the reaction mixture. The solid was washed with ethanol and recrystallized from dimethylformamide-water, yielding 4.5 gm. of 1-methyl-3-nitro-4-pyrazolecarboxylic acid, 5-nitrofurfurylidene hydrazide, m.p. 225°–227° C. dec.

In making out bis compounds, wherein two 3-nitropyrazole nuclei are connected through a common 1-substituent, it is frequently convenient to carry out the 4-substituent reaction before the joining 1-substituent reaction. For example, the following two-stage reaction is effective.

EXAMPLE 22

3-nitro-4-pyrazolecarboxamide sodium salt

A solution was made of 8 gm. of 1-sodium salt of 3-nitro-4-pyrazolecarbonitrile in methanol, and 75 ml. of 15% $H_2O_2$ was added, followed by 5 ml. of 6N NaOH. The reaction mixture was heated to 45° C., at which point external cooling was needed to maintain the mixture at 45°–50° C. After the exothermic reaction had subsided, the mixture was held at 45°–50° C. and stirred for 4 hours. Then the mixture was cooled and the methanol was evaporated under vacuum. The liquid remaining was cooled in an ice bath and the product was separated by filtration and dried under vacuum. The dry product was determined to be 8 gm. of 3-nitro-4-pyrazolecarboxamide sodium salt, m.p. >300° C.

EXAMPLE 23

1,1'-(2,5-cyclohexadien-1,4-ylene)-bis(3-nitro-4-pyrazolecarboxamide

A suspension was made of 5.34 gm. of 3(5)-nitro-4-pyrazolecarboxamide sodium salt, made as in Example 22 above, in 100 ml. of acetonitrile. To the suspension was added 4 gm. of propargyl bromide and 2.5 gm. of anhydrous $Na_2CO_3$. A small quantity of water was then added to the mixture. The reaction mixture was stirred at room temperature for 24 hours. The mixture was then poured into 500 ml. of water and extracted with ethyl acetate. The organic layer was washed with cold saltwater and dried over $MgSO_4$. Evaporation of the solvent under vacuum, and decolorization and recrystallization of the crude solid from isopropanolmethanol yielded 1.6 gm. of 1,1'-(2,5-cyclohexadien-1,4-ylene)-bis(3-nitro-4-pyrazolecarboxamide),m.p. 128°–130° C. dec.

The following example shows the synthesis of one of our 4-thiadiazolyl compounds.

EXAMPLE 24

2-amino-5-(1-methyl-3-nitro-4-pyrazolyl)-1,3,4-thiadiazole

A suspension was made of 4.55 gm. of thiosemicarbazide, 100 ml. of 1,2-dimethoxyethane, and 4 gm. of pyridine. A solution of 9.48 gm. of 1-methyl-3-nitro-4-pyrazolecarbonyl chloride in 50 ml. of 1,2-dimethoxyethane was added dropwise with stirring under reflux for 15 hours. Then the mixture was cooled to room temperature and filtered. The solid was washed with cold water and dried under vacuum yielding 9 gm. of 1-(1-methyl-3-nitro-4-pyrazolylcarbonyl)-3-thiosemicarbazide, m.p. 206°–208° C.

Five hundred milligrams of the above product was added to 15 ml. of concentrated sulfuric acid and stirred at 70°–75° C. for 16 hours, forming a yellow solution. The reaction mixture was cooled to room temperature and cautiously poured into ice water. Some insoluble material was filtered off and the filtrate made basic (pH 8-9) by the addition of 50% NaOH. The orange solid which precipitated was filtered off, washed with cold water and dried under vacuum at 100° C. Recrystallization from DMF-methanol yielded 250 mg. of 2-amino-5-(1-methyl-3-nitro-4-pyrazolyl)-1,3,4-thiadiazole, m.p. 275°–277° C. dec.

The antimicrobial, particularly antibacterial, activity of our new compounds is their most important property, and is shared by all the compounds. The examples below show specific data demonstrating the antimicrobial efficacy of many of our compounds. Many of our 3-nitropyrazoles also possess herbicidal, parasiticidal, and other biological efficacies which will be discussed in detail below.

All of our 3-nitropyrazoles have important biological activity, as will be illustrated in detail below. Despite the high effectiveness of the series of compounds as a whole, it is possible to identify the following preferred compounds. The compound numbers are from the listing above.

16. 1-allyl-3-nitro-4-pyrazolecarboxamide
32. 1-(2-hydroxyethyl)-3-nitro-4-pyrazolecarboxamide
34. 1-(2-ethoxyethyl)-3-nitro-4-pyrazolecarboxamie
58. 1-(2-hydroxyethyl)-N-methyl-3-nitro-4-pyrazolecarboxamide
80. 2-(4-carbamoyl-3-nitropyrazol-1-yl)ethyl acetate A second group of preferred compounds include the following.

33. 1-(2-chloroethyl)-3-nitro-4-pyrazolecarbonitrile
35. 1-(2-ethylsulfonylethyl)-3-nitro-4-pyrazolecarboxamide
59. 1,1'-(2,5-cyclohexadien-1,4-ylene)-bis(3-nitro-4-pyrazolecarboxamide)
69. 1-(2-hydroxypropyl)-3-nitro-4-pyrazolecarboxamide
77. [2-(4-carbamoyl-3-nitropyrazol-1-yl)ethyl] phenyl carbonate
81. 3-nitro-1-vinyl-4-pyrazolecarboxamide
83. 1-(3-chloropropyl)-3-nitro-4-pyrazolecarbonitrile
90. 1-cyclopropylmethyl-3-nitro-4-pyrazolecarboxamide
102. 2-amino-5-(1-methyl-3-nitro-4-pyrazolyl)-1,3,4-thiadiazole The preferred compounds stand out among the many biologically-effective compounds of our invention because of their outstanding efficacy in the control of a variety of microorganisms and diseases.

Our compound, 1-(2-hydroxyethyl)-3-nitro-4-pyrazolecarboxamide, has been extensively tested in vitro to determine the range of microorganisms against which it is active. The table of data below reports the minimum inhibitory concentration (MIC) at which the compound is effective in controlling a variety of microorganisms in a standard tube dilution test system. The MIC is reported as micrograms of compound per milliliter.

| | |
|---|---|
| *Escherichia coli* | 3.12 |
| *Salmonella* sp. | 3.12 |
| *Arizona hinshaw* (paracolon) | 6.25 |
| *Pseudomonas* sp. | 12.50 |
| *Pasteurella multocida* Cattle Isolates | < 1.56 |
| Turkey Isolates | >50.00 |
| Swine Isolate | >50.00 |
| Swine Isolate | 6.25 |
| *Pasteurella hemolytica* | < 1.56 |
| *Vibrio coli* | 6.25 |
| *Treponema hyodysenteriae* | 3.12 |
| *Mycoplasma gallisepticum* | 0.78 |
| *Mycoplasma synoviae* | 50.00 |
| *Mycoplasma hyosynoviae* | 50.00 |
| *Mycoplasma hyorhinis* | 50.00 |
| *Mycoplasma hyopneumoniae* | 50.00 |
| *Bordetella bronchiseptica* | 25.00 |
| *Stapylococcus* sp. | 3.12 |
| *Streptococcus* sp. | 25.00 |
| *Streptococcus* sp. (group E) | 1.56 |
| *Erysipelas insidiosa* | >50.00 |
| *Leptospira* (5 serotypes) | >100.00 |
| *Hemophilus gallinarum* | 0.78 |
| *Hemophilus somnus* | >100.00 |
| *Clostridium perfringens* (8 avian isolates) | 25–50 |
| *Salmonella typhimurium* 1503 (poult intestine) | < 1.56 |
| *Salmonella heidelburg* 1593 (turkey pancreas) | < 1.56 |
| *Salmonella typhimurium* 1335 (turkey intestine) | 6.25 |
| *Salmonella pullorum* 9-25 | < 1.56 |
| *Salmonella pullorum* 9-27 | < 1.56 |
| *Salmonella pullorum* Ill. | < 1.56 |

Further in vitro studies of the above compound have been conducted by the agar dilution technique. The results of the agar dilution studies are reported below as the MIC in micrograms in milliliter.

| | |
|---|---|
| Citrobacter freundii | 8.0 |
| Enterobacter cloacae and aerogenes | 32.0 |
| Escherichia coli | 8.0 |
| Hemophilus influenzae | 4.0 |
| Proteus sp. | >128.0 |
| Serratia sp. | 32.0 |
| Staphylococcus aureus | 8.0–16.0 |
| Streptococcus pyogenes | 32.0 |
| Streptococcus sp. (group D) | 32.0 |
| Diplococcus pneumoniae | 2.0 |
| Mima polymorpha | 2.0 |
| Pseudomonas aeruginosa | 128.0 |
| Salmonella typhosa | 2.0 |
| Klebsiella pneumoniae (2 isolates) | 4.0, 32.0 |
| Shigella sp. | 16.0 |
| Alkaligenes fecalis | 128.0 |

The other preferred compounds of our invention have also been thoroughly tested in the in vitro tube dilution test. The table below reports the MIC's, in micrograms per milliliter, at which certain of our compounds were found to be effective against the named microorganisms.

| Organisms | Compound Number | | | |
|---|---|---|---|---|
| | 16 | 34 | 58 | 80 |
| Salmonella heidelburg 1593 | 25.0 | — | 12.5 | 12.5 |
| Salmonella typhimurium 1335 | 6.25 | — | 12.5 | 12.5 |
| Salmonella pullorum Ill. | <1.56 | — | 3.12 | <1.56 |
| Staphylococcus aureus 3055 | 10.0 | 100.0 | 10.0 | 10.0 |
| Escherichia coli 0127 | 100.0 | — | — | 100.0 |
| Vibrio coli 3811 | 3.12 | 50 | 25.0 | 12.5 |
| Salmonella dublin | 6.25 | 25.0 | 12.5 | 12.5 |
| Pseudomonas sp. | 12.5 | 50.0 | 25.0 | 25.0 |
| Staphylococcus 1130 | 6.25 | 6.25 | 12.5 | 3.12 |
| Mycoplasma gallisepticum 38502 | 50.0 | 50.0 | 6.25 | 25.0 |
| Mycoplasma hyorhinis | 50.0 | 50.0 | — | 50.0 |
| Pasteurella multocida | — | 25.0 | 0.78 | 25.0 |

Other compounds of our invention have also been tested in the tube dilution test and shown to have in vitro activity against a number of microorganisms. The table below reports tests of a number of exemplary compounds against exemplary microorganisms. The compounds are identified by their numbers in the listing above. The data are reported as the MIC in micrograms per milliliter against the named exemplary microorganisms.

| Compound No. | Streptococcus sp. 80 | Pasteurella multocida | Salmonella dublin | Vibrio coli 3811 | Mycoplasma gallisepticum | Escherichia coli | Staphylococcus aureus sp. 1130 |
|---|---|---|---|---|---|---|---|
| 1 | 100.0 | — | 100.0 | 12.5 | >50.0 | 100.0 | 100.0 |
| 2 | 50.0 | — | 50.0 | 25.0 | 6.25 | 50.0 | 50.0 |
| 3 | 100.0 | — | 6.25 | 6.25 | 50.0 | 12.5 | 12.5 |
| 4 | >50.0 | 12.5 | 50.0 | 6.25 | 50.0 | 50.0 | >50.0 |
| 5 | >50.0 | 3.12 | >50.0 | 6.25 | 25.0 | >50.0 | 3.12 |
| 9 | 50.0 | >50.0 | 6.25 | 6.25 | >50.0 | 12.5 | 6.25 |
| 10 | 6.25 | 25.0 | >50.0 | 50.0 | 50.0 | 50.0 | 6.25 |
| 18 | 50.0 | 12.5 | 12.5 | 50.0 | 6.25 | 12.5 | 6.25 |
| 30 | 100.0 | — | 100.0 | 100.0 | 50.0 | 100.0 | 100.0 |
| 31 | 50.0 | — | 50.0 | 12.5 | 50.0 | 50.0 | 50.0 |
| 33 | 100.0 | — | 100.0 | 12.5 | >50.0 | 100.0 | 100.0 |
| 35 | 25.0 | 6.25 | 50.0 | 50.0 | >50.0 | 50.0 | 3.12 |
| 48 | >50.0 | 0.39 | >50.0 | 50.0 | 50.0 | >50.0 | 25.0 |
| 52 | 50.0 | 12.5 | 3.12 | 25.0 | >50.0 | 3.12 | >1.56 |
| 55 | 50.0 | — | 6.25 | — | — | 12.5 | 6.25 |
| 59 | >50.0 | 3.12 | 3.12 | 12.5 | 3.12 | 3.12 | 1.56 |
| 60 | >50.0 | 25.0 | >50.0 | >50.0 | 50.0 | >50.0 | >50.0 |
| 61 | 50.0 | — | 50.0 | — | 12.5 | 50.0 | 50.0 |
| 62 | 50.0 | 6.25 | 3.12 | 12.5 | 1.56 | 6.25 | 50.0 |
| 63 | >50.0 | 25.0 | 12.5 | 25.0 | 6.25 | 50.0 | 50.0 |
| 64 | >50.0 | 50.0 | 12.5 | >50.0 | 50.0 | 25.0 | 50.0 |
| 65 | >50.0 | 50.0 | 12.5 | 50.0 | 50.0 | 12.5 | 50.0 |
| 66 | 25.0 | 12.5 | >50.0 | >50.0 | 50.0 | 50.0 | 25.0 |
| 67 | 50.0 | 25.0 | 50.0 | 50.0 | 50.0 | 50.0 | 50.0 |
| 68 | 50.0 | 12.5 | 50.0 | 12.5 | 25.0 | 50.0 | 25.0 |
| 70 | 100.0 | — | 100.0 | 12.5 | >50.0 | 100.0 | 100.0 |
| 71 | >50.0 | >50.0 | >50.0 | >50.0 | 0.39[1] | >50.0 | >50.0 |
| 72 | >50.0 | >50.0 | >50.0 | >50.0 | >50.0 | >50.0 | >50.0 |
| 73 | 50.0 | 12.5 | 50.0 | 25.0 | 50.0 | 50.0 | 50.0 |
| 74 | 50.0 | — | 12.5 | 0.39 | 0.78 | 6.25 | 1.56 |
| 75 | >50.0 | 25.0 | 25.0 | 12.5 | >50.0 | 50.0 | 12.5 |
| 81 | 25.0 | 1.56 | 1.56 | 25.0 | 1.56 | 1.56 | 1.56 |
| 82 | 50.0 | 50.0 | 50.0 | 50.0 | 25.0 | 50.0 | 50.0 |
| 83 | >50.0 | >50.0 | >50.0 | 25.0 | 50.0 | >50.0 | >50.0 |
| 84 | 50.0 | 25.0 | 50.0 | 25.0 | 50.0 | 50.0 | 50.0 |
| 85 | >50.0 | >50.0 | >50.0 | 50.0 | 3.12 | >50.0 | >50.0 |
| 86 | >50.0 | >50.0 | >50.0 | 25.0 | 50.0 | >50.0 | >50.0 |
| 88 | >50.0 | 6.25 | >50.0 | 50.0 | 3.12 | 50.0 | >50.0 |
| 90 | >50.0 | 25.0 | 50.0 | 50.0 | >50.0 | 50.0 | 50.0 |
| 91 | 50.0 | 12.5 | >50.0 | 12.5 | >50.0 | >50.0 | >50.0 |
| 92 | 50.0 | 0.78 | >50.0 | 6.25 | 12.5 | >50.0 | 6.25 |
| 93 | 6.25 | <1.56 | 6.25 | 50.0 | 12.5 | 12.5 | 3.12 |
| 94 | 25.0 | <1.56 | 25.0 | <1.56 | 6.25 | 25.0 | 6.25 |
| 95 | 50.0 | 3.12 | 25.0 | <1.56 | 12.5 | >50.0 | <1.56 |
| 96 | >50.0 | 12.5 | 3.12 | 25.0 | 25.0 | 6.25 | <1.56 |
| 97 | >50.0 | 25.0 | >50.0 | 12.5 | 25.0 | >50.0 | >50.0 |
| 102 | 50.0 | — | 12.5 | 12.5 | 12.5 | 12.5 | 6.25 |

[1] M. synoviae

Those skilled in the veterinary medical art are aware that antimicrobial compounds often control diseases caused by microorganisms which the compounds control in vitro. We have tested our antimicrobial 3-nitropyrazoles in laboratory and economic animals, as well as in plants, and have found that the compounds control a number of important diseases.

Exemplary compoumds of our invention have also been tested to determine their ability to control other microorganisms in vivo, and to determine their biological properties other than their microbiocidal properties.

Some 3-nitropyrazoles have been used against *Trypanosoma cruzi* in rodents. The 3-nitro-1-vinyl-4-pyrazolecarboxamide killed 91 percent of *T. cruzi* of the BHC/10 strain when administered at 12.5 mg./kg. for 10 days.

The herbicidal compounds of our invention have shown the ability to control undesired plants at levels as low as 1 lb./acre. Herbicidal activity is obtained when the 3-nitropyrazole herbicide is applied to the plants to be controlled in the conventional manner, by direct application as a spray or dry formulation to the plant or its supporting soil. For example, 1-ethyl-3-nitro-4-pyrazolecarbonitrile kills large crabgrass when applied to the foliage of the growing plant at 1 lb./acre.

The tests reported below demonstrate the unusual efficacy of our 3-nitropyrazoles in preventing and treating both natural and induced infections of woody and soft plants, and of a variety of animals. The examples report efficacy in standard laboratory animals, as well as in poultry, cattle, and swine. Both percutaneous and oral administration of our compounds to animals have given outstanding disease control. We have shown that our compounds are generally useful in the control of harmful microorganisms, and in the control of diseases caused by harmful microorganisms, and expecially by harmful bacteria, as well as in the control of harmful parasites.

EXAMPLE 25

Fire Blight of Pear

An in vivo test was conducted against the fire blight organism, *Erwinia amylovora*. Plants infected with *E. amylovora* were sprayed with aqueous dispersions containing 100 ppm. and 500 ppm. of the test compounds. The infected plants were observed in the greenhouse, and the results reported as percent control of fire blight. The compounds are identified below by their compound numbers in the above listing.

| Compound | Percent Control | |
| No. | 100 ppm. | 500 ppm. |
| --- | --- | --- |
| 3 | 25% | 75% |
| 16 | 100% | 60% |
| 32 | 50% | 92% |
| 34 | 33% | 66% |
| 80 | 33% | 50% |
| 81 | 100% | 60% |

The test reported above demonstrates the ability of a number of our 3-nitropyrazoles, of diverse substitution patterns, to control an important plant pathogen.

Our compound, 1-(2-hydroxyethyl)-3-nitro-4-pyrazolecarboxamide, was also tested against natural and induced infections of *E. amylovora* on field-grown pear trees. Application of aqueous dispersions of the 3-nitropyrazole at rates from 100 to 800 ppm. controlled fire blight on the pear trees.

EXAMPLE 26

Fire Blight of Apple

A typical test of one of our compounds against an induced *E. amylovora* infection of McIntosh apple seedlings will be reported. The compound, [2-(4-carbamoyl-3-nitropyrazol-1-yl)ethyl] phenyl carbonate, was sprayed on the seedlings as an aqueous dispersion at the concentrations shown below. Four replicate trees were used per treatment. After the spray had dried, each tree was challenged by punching a hole through the midvein at the tip of one leaf per plant, and placing a drop of an *E. amylovora* culture in the hole.

After 6 days, the trees were observed, and the control of the infection was rated on the following scale.

1 = disease symptoms in main stem
2 = disease symptoms in petiole
3 = disease symptoms in the leaf only
4 = complete control of disease The results are shown below as the mean disease control rating.

| Concentration | Mean Rating |
| --- | --- |
| 0 | 1.0 |
| 200 ppm. | 2.5 |
| 400 | 3.5 |
| 600 | 3.0 |
| 800 | 3.4 |
| 1000 | 3.5 |
| 1200 | 3.5 |

The results above shown that our compound provided effective control of a very severe induced infection.

EXAMPLE 27

Aster Yellows Disease

The following data report a test of an exemplary compound against aster yellows disease. The compound, [2-(4-carbamoyl-3-nitropyrazol-1-yl)ethyl] phenyl carbonate, was applied to aster plants as an aqueous dispersion at concentrations shown below. Two plants were sprayed with each concentration. Each pair of plants was placed in a wire mesh cage, and four leafhoppers infected with the mycoplasma which causes aster yellows were placed in each cage. After 20 days, the plants were observed and disease control was rates as the percent of the plants' surface affected by the disease.

| Concentration | Percent Infection |
| --- | --- |
| 0 (Blank) | 100 |
| 200 | 0 |
| 400 | 25 |
| 800 | 0 |

Our compound gave excellent control of the mycoplasma-induced, vector-spread plant disease, aster yellows.

EXAMPLE 28

Tests In Mice

Groups of laboratory mice were inoculated with *E. coli* or with *Streptococcus pyogenes*. The 3-nitropyrazoles were administered in two different modes to the infected mice. In one group of tests, the compound was administered in two subcutaneous doses of 83 mg./kg.

each, given 1 and 5 hours after the mice were inoculated with the organism. The mice were observed, and the results reported below as the number of days the treated mice survived the challenge.

In the other group of tests, the dose of each compound which allowed 50 percent of the treated mice to survive the challenge was determined. Again, the compound was administered in subcutaneous divided doses, 1 and 5 hours post-inoculation.

| Compound | Days Survived | | $ED_{50}$, mg./kg. × 2 | |
|---|---|---|---|---|
| Number | S. pyogenes | E. coli | S. pyogenes | E. coli |
| Blank | 1 | 1 | — | — |
| 32 | 5.0 | 7.0 | 53.7 | 19.6 |
| 34 | 5.0 | 7.0 | — | >41 |
| 35 | 7.0 | 1.0 | 36.2 | — |
| 58 | 1.8 | 7.0 | — | 40 |
| 61 | 1.0 | — | >83 | 68 |
| 88 | 2.0 | 4.8 | — | — |

Some of the 3-nitropyrazoles were also administered to mice infected with *P. multocida*. Tests were conducted in which the pyrazoles were administered both by injection and in the drinking water.

The table below reports results of tests in which the compound was administered in the water. Groups of 10 standardized white mice were segregated, and each mouse was infected by injecting a broth culture of *P. multocida* subcutaneously. The administration of the test compounds was begun at the same time the mice were infected by adding a known amount of the test compound to the drinking water of the mice. One group of infected control mice received no treatment. The mice were observed, and the test was concluded at the end of 7 days. The number of mice in each group which survived the *P. multocida* infection was recorded.

| Compound | Dosage Rate gm./gal. | Survival |
|---|---|---|
| 1-(2-hydroxyethyl)-3-nitro-4-pyrazole-carboxamide | 0.1 | 8/10 |
| | 0.2 | 10/10 |
| 2-(4-carbamoyl-3-nitropyrazol-1-yl)-ethyl acetate | 0.1 | 9/10 |
| | 0.2 | 6/10 |
| Infected Controls | | 2/10 |

A second test was conducted in much the same way, except that the 3-nitropyrazole was injected to the treated mice subcutaneously at the same time they were infected with the *P. multocida* culture.

| Treatment | Survival |
|---|---|
| 1-(2-hydroxyethyl)-3-nitro-4-pyrazolecarboxamide | |
| 2.5 mg./kg. | 8/10 |
| 2-(4-carbamoyl-3-nitro-pyrazol-1-yl)ethyl acetate | |
| 2.5 mg./kg. | 4/10 |
| 5.0 mg./kg. | 3/10 |
| 10.0 mg./kg. | 8/10 |
| 25.0 mg./kg. | 9/10 |
| Infected Controls | 2/10 |

Both oral and percutaneous administration of the 3-nitropyrazole compounds protected the infected mice from a very severe pasteurella infection.

The following two examples report tests against bovine respiratory diseases caused by pasteurella organisms. The etiology and consequences of the diseases will be briefly described.

It is belived that the pasteurellae, particularly *Pasteurella multocida* and *P. hemolytica*, are important and probably primary causes of bovine pneumonia and other respiratory disorders. Collier, Significance of Bacteria In Bovine Respiratory Disease, J.A.V.M.A. 153, 1645–1651 (1968). A number of different respiratory diseases, which have in common a pasteurella infection, afflict cattle.

Bovine pasteurella infections often occur in combination with other infections. For example, cattle with shipping fever typically have simultaneously an acute bacterial pneumonia, intestinal infections, and infections of the sinuses and nasal passages. In most cases, it is the respiratory aspect of the shipping fever complex which causes the worst injuries and even death of the afflicted animals.

A somewhat related affliction of young calves is known as pneumoenteritis complex. It is a combination of a bacterial pneumonia and an intestinal infection of *Escherichia coli* and salmonella species. The infected calves fail to gain weight normally, are delayed and retarded in their development, and may die.

EXAMPLE 29

Pneumoenteritis Complex Disease in Calves

Our compound, 1-(2-hydroxyethyl)-3-nitro-4-pyrazolecarboxamide, was evaluated in the control of a naturally-occurring pneumoenteritis complex infection of calves. The infection is a combined pneumonia-like infection involving mostly pasteurella species, and an enteric infection primarily caused by *E. coli* and salmonellae. A group of 24 calves was allocated randomly into three treatment groups. The average weights of the treatment groups were nearly identical at the start of the experiment. The calves were housed in quarters which were kept as clean as typical calf quarters, but in which calves suffering from pneumoenteritis complex had previously been housed. The calves were observed for 56 days. One group was a control group, and was fed on a typical milk replacer diet. The other two groups received 200 mg. and 400 mg. per day respectively of the 3-nitropyrazole compound, mixed in their milk replacer diets.

The calves were carefully observed daily to detect signs of illness as quickly as such signs appeared. The calves were weighed at weekly intervals. Various organs were removed from the calves which died during the experiment, and cultures were prepared from the organs to identify microorganisms. At the end of the 56-day experiment, cultures were prepared from nasal and rectal swabs of the surviving calves, and microorganisms in the cultures were identified.

The table below shows the mortality, and the average weight gain of the survivors of the experiment.

| Treatment | Avg. Wt. Gain | Mortality |
|---|---|---|
| 200 mg./day/calf (3–5 mg./kg./day) | 36.6 lbs. | 1/8 |
| 400 mg./day/calf (6–10 mg./kg./day) | 55.3 lbs. | 1/8 |
| Control | 6.2 lbs. | 7/8 |

The nature of the infection was shown by microorganisms recovered from the seven control calves which died during the experiment. Salmonella species and *E. coli* were found in all of the calves. *Pasteurella hemolytica* was isolated in the lungs of four of the dead calves, indicating the respiratory infections from which the calves suffered.

*P. multocida* or *hemolytica* was found in nasal swabs of 11 of the 14 surviving treated calves, and *E. coli* was recovered in rectal swabs of 12 of the surviving calves. Nevertheless, the calves treated with the 3-nitropyrazole performed approximately normally in spite of the very severe infection to which they were exposed.

The test reported below was conducted in general identically with the test above. All of the calves used in the test were approximately 3 days old when the test began, and the test ran for 56 days.

The treated group received 200 mg./day/calf (about 3-5 mg./kg./day) of 1-(2-hydroxyethyl)-3-nitro-4-pyrazolecarboxamide, which was administered in the calves' milk replacer diet.

The table below reports the average weight gain of the surviving animals and the mortality of the calves in each group.

| Treatment | Avg. Wt. Gain | Mortality |
|---|---|---|
| 200 mg./day/calf | 52.1 lbs. | 1/8 |
| Untreated Controls | 49.0 lbs. | 5/8 |

*E. coli, P. hemolytica*, diplococuss species, and staphylococcus species were isolated from the calves which died during the test. Of the calves treated with the 3-nitropyrazole, 6 of the survivors were found to have *P. multocida* organisms in their nasal secretions, and *E. coli* was found in rectal swabs of all of the surviving treated calves. Nevertheless, the treated calves, protected by the 3-nitropyrazole treatment, experienced only about 12 percent mortality.

EXAMPLE 30

Pasteurella Pneumonia in Calves

An experiment was conducted to determine the ability of 1-(2-hydroxyethyl)-3-nitro-4-pyrazolecarboxamide to prevent pasteurella pneumonia in calves. Nine calves were allocated to three groups. Two of the groups were held as infected control groups, and the third group was treated with the test compound.

The temperature of all of the calves were recorded for two weeks before the pasteurella challenge was administered, to establish a temperature base line. The average temperature of all of the calves during the pre-challenge time was 102.2° F. The temperatures of the calves were recorded daily after the challenge, to indicate the extent of infection of each calf.

The first step in the test was to administer 200,000 ascaris ova, as a single oral dose, to each calf. Ascaris larvae migrating through the lungs leave inflamed sites which insure that the pasteurella challenge results in pneumonia. The calves were observed and their temperatures were recorded each day from the administration of the ascaris ova until the end of the experiment.

Six days after the ova were administered, administration of the test compound to the three calves of the treated group began. Each calf received daily intramuscular injections of the compound at a rate of 25 mg. per kg. of body weight for five days.

The day after the first administration of the test compound, each calf was challenged with an aerosol dispersion of a mixture of *Pasteurella multocida* and *P. hemolytica* broth cultures. Both organisms are known to be involved in bovine pneumonia.

The table below shows the average temperatures of the calves of the three groups during the post-challenge period.

| Treatment | Average Temperature |
|---|---|
| 3-nitropyrazole | 102.7° F. |
| Infected Control | 104.9° F. |
| Infected Control | 105.1° F. |

The temperatures show that the treated animals contracted only a very mild pasteurella infection. Indeed, most of the calves had a temperature on one or more prechallenge days as high as the average post-challenge temperature of the treated animals. In contrast, the infected control animals had temperatures consistently two or more degrees above normal after the challenge.

The calves were observed for 8 days after the challenge, and then all of the calves were killed and necropsied. The lungs were examined for pneumonic lesions, and were cultured to identify pasteurella organisms.

The observations and cultures confirmed the favorable results indicated by the temperature data. No pasteurellae were identified in the lungs of any of the three animals treated with the nitropyrazole. All six of the infected control animals were culturally positive for *P. multocida, P. hemolytica*, or both. The cultural identification of pasteurella organisms proved that the high temperatures of the infected control animals were in fact caused by pasteurella pneumonia.

Physical examination of the lungs of the treated animals revealed minor consolidation or emphysema in areas of the lungs, which was consistent with a minor respiratory infection. All six of the infected control animals had large severe areas of consolidation or emphysema. One animal had adhesions of the lungs, and another had a marked amount of serous fluid in the chest cavity. Four of the six infected control animals had from 60 to 100 percent consolidation of major lobes of the lungs.

The test shows extremely successful control of bovine bacterial pneumonia. The infected control animals contracted typical cases of severe pneumonia, with extensive consolidation of the lungs evident in most of the animals and abnormally high temperatures of all animals. The nitropyrazole prevented severe infection of the treated animals, and held the lung involvement to a very mild emphysema and consolidation.

Results of testing compounds of our invention against a number of poultry diseases are presented in the seven examples immediately following. Each disease will be briefly described.

Blackhead is a poultry disease caused by a protozoa, *Histomonas meleagridis*. It is extrememly damaging in turkeys, in which it often causes 100 percent mortality of an infected flock, and only somewhat less injurious to chickens. The protozoa is often transmitted as a parasite in eggs of the cecal worm *Heterakis gallinae*, in which eggs it is able to live in waste and on the soil for extended periods of time.

EXAMPLE 31

Blackhead in Poultry

One- to three-week-old chicks and turkey poults were obtained from homogeneous source flocks and allocated into treatment groups. Some groups were held as infected, untreated controls, and other groups were treated with 3-nitropyrazoles by administering the compounds in the birds' feed. Various concentrations of the pyrazoles were administered to determine the least concentration which protected the birds. A few days after the administration of medicated feed began, all of the birds were challenged by rectally administering a suspension of at least 5,000 H. meleagridis protozoa per chick. The challenge organisms had been originally obtained from infected chickens, and were grown in vitro to provide a supply of organisms for testing.

The birds were held for about seven days after the challenge was administered, during which time the administration of pyrazole-medicated feed was continued. Then all of the chicks, including the untreated, infected controls, were sacrificed and necropsied. The cecum and the liver of each bird were examined for characteristic H. meleagridis lesions.

Each treatment was categorized as active or inactive, depending on whether or not the treatment significantly reduced the number or severity of lesions, as compared with the lesions in infected control birds.

Results of tests of typical compounds are shown below. For each compound, the lowest feed concentration which gave an active response is indicated. While feed consumption data were not taken during the tests, the birds ate at such a rate that a feed concentration of .02 percent is equivalent to a treatment rate of about 10 mg./kg./day.

| Compound No. | Active Level |
|---|---|
| 2 | .02% in chicks |
| 3 | .02% in chicks |
| 16 | .02% in turkeys |
| 17 | .0067% in chicks; .02% in turkeys |
| 32 | .02% in turkeys |
| 34 | .02% in turkeys |
| 65 | .02% in chicks |
| 77 | .02% in chicks |
| 90 | .02% in chicks |

The typical tests reported above showed that administration of the pyrazoles controlled infections of H. meleagridis in poultry. Both chickens and the more sensitive turkeys were protected, and moderate treatment rates were sufficient.

A number of economically damaging diseases of poultry are caused by salmonella organisms. Salmonellosis of poultry includes, besides less important diseases, paratyphoid, fowl typhoid, and pullorum disease.

The etiology of the salmonella diseases is by no means clear. Salmonella typhimurium is perhaps the most common cause of paratyphoid; S. gallinarum, of fowl typhoid; and S. pullorum, or pullorum disease. All of the salmonellae which have been implicated in the salmonellosis poultry diseases are much alike and share many of the same characteristics.

EXAMPLE 32

Salmonellosis in Chickens

A number of our 3-nitropyrazoles have been tested against an induced infection of Salmonella typhimurium in day-old chicks. The test was conducted by administering a single injection of 60 mg./kg. of the compounds to each of five chicks. The following day, the chicks were challenged by the subcutaneous injection of a dispersion of S. typhimurium organisms sufficient to kill most or all of the untreated control chicks.

The chicks were observed for seven days, and the result of the test was reported as the number of chicks in each five-chick group which survived the challenge. Some of the compounds were tested more than once, in which instances the data are reported as the total survivors from the multiple treatment groups. Untreated, challenged control groups of chicks were tested together with each batch of groups of chicks to which test compounds were administered. Since the mortality of the untreated control chicks varied somewhat from one group of tests to another, results of the untreated control groups are reported below with each test.

| Compound Tested | Survival | Untreated Control Survival |
|---|---|---|
| 1-(2,2-diethoxyethyl)-3-nitro-4-pyrazolecarboxamide | 4/5 | 0/18 |
| 1-(2-hydroxypropyl)-3-nitro-4-pyrazolecarboxamide | 10/10 | 1/20 |
| 1-(3-hydroxypropyl)-3-nitro-4-pyrazolecarboxamide | 7/10 | 1/20 |
| 1-allyl-3-nitro-4-pyrazolecarboxamide | 10/10 | 1/20 |
| 2-(4-carbamoyl-3-nitropyrazol-1-yl)ethyl acetate | 7/10 | 0/20 |
| 1-(2-butenyl)-3-nitro-4-pyrazolecarboxamide | 3/5 | 0/10 |
| 1-(2-methoxyethyl)-3-nitro-4-pyrazolecarboxamide | 7/10 | 2/20 |
| 1-isopropyl-3-nitro-4-pyrazolecarboxamide | 6/10 | 2/20 |
| 1-(2-methylsulfonylethyl)-3-nitro-4-pyrazolecarboxamide | 2/5 | 1/10 |
| 1-cyclopropylmethyl-3-nitro-4-pyrazolecarboxamide | 4/5 | 0/10 |
| 1-(2-ethylsulfonylethyl)-3-nitro-4-pyrazolecarboxamide | 8/10 | 0/20 |
| 1-(3-chloropropyl)-3-nitro-4-pyrazolecarbonitrile | 4/5 | 1/10 |
| 1-(2-hydroxyethyl)-N-methyl-3-nitro-4-pyrazolecarboxamide | 9/10 | 1/20 |
| 1-(2-hydroxyethyl)-3-nitro-4-pyrazolecarboxamide | 14/15 | 1/30 |
| N,1-dimethyl-3-nitro-4-pyrazolecarboxamide | 7/10 | 0/20 |
| 3-nitro-1-propyl-4-pyrazolecarboxamide | 4/5 | 0/10 |
| [2-(4-carbamoyl-3-nitropyrazol-1-yl)ethyl]phenyl carbonate | 8/10 | 0/20 |
| 1-(2-chloroethyl)-3-nitro-4-pyrazolecarboxamide | 8/10 | 0/10 |
| 3-nitro-1-(2-oxopropyl)-4-pyrazolecarboxamide | 5/5 | 0/10 |
| 1-(2-bromoethyl)-3-nitro-4-pyrazolecarboxamide | 5/5 | 0/10 |
| 1-benzyl-3-nitro-4-pyrazolecarboxamide | 7/10 | 3/20 |
| 1-(2-ethoxyethyl)-3-nitro-4-pyrazolecarboxamide | 2/5 | 0/10 |
| 1-(2-hydroxyethyl)-3-nitro-4-pyrazolecarbonitrile | 12/15 | 0/30 |
| 1-(2-chloroethyl)-3-nitro-4-pyrazolecarbonitrile | 4/5 | 0/10 |
| 2-(4-carbamoyl-3-nitropyrazol-1-yl)ethyl 3,4-dichlorobenzoate | 5/5 | 3/10 |
| 2-(4-carbamoyl-3-nitropyrazol-1-yl)ethyl 3-chlorobenzoate | 4/5 | 3/10 |
| [2-(4-carbamoyl-3-nitropyrazol-1-yl)ethyl]carbamate | 5/5 | 0/10 |
| 1-(2-ethoxyethyl)-3-nitro-4-pyrazolecarbonitrile | 4/5 | 3/10 |
| [2-(4-carbamoyl-3-nitropyrazol-1-yl)ethyl] ethyl |  |  |

| Compound Tested | Survival | Untreated Control Survival |
|---|---|---|
| carbonate | 2/5 | 1/10 |
| 1-(3-chloropropyl)-3-nitro-4-pyrazolecarboxamide | 2/5 | 1/10 |
| [2-(4-carbamoyl-3-nitro-pyrazol-1-yl)ethyl]p-toluate | 5/5 | 1/10 |

The consistent control of induced salmonellosis, evidenced by the reduced mortality of the treated chicks, is very apparent. Many of the compounds gave good survival rates in the face of 100 percent kill of the control birds. No compound gave less than a 40 percent survival rate, and no compound allowed a survival rate lower than 250 percent of the survival of the control birds tested with it.

Additional compounds which have protected at least three chicks of the 5-bird treated group from salmonella challenge include, for example, 2-(1-methyl-3-nitro-4-pyrazolyl)-5-methylamino-1,3,4-thiadiazole, 1,1′-(2,5-cyclohexadien-1,4-ylene)-bis(3-nitro-4-pyrazolecarboxamide), N-butyl-1-(2-hydroxyethyl)-3-nitro-4-pyrazolecarboxamide, and 2-amino-5-(1-methyl-3-nitro-4-pyrazolyl)-1,3,4-thiadiazole.

Further tests against salmonellosis infections have also been conducted.

EXAMPLE 33

Salmonella typhimurium in Chickens

The tests were conducted by administering a compound in the feed of chicks which were one day old when the tests began. The day after beginning administration of the compound, the chicks, together with untreated control chicks, were challenged by administering a tryptose broth culture of *S. typhimurium* orally to the chicks. The culture was placed in the cage waterer and the chicks were allowed to drink it freely.

The pyrazole-medicated feed was administered to the chicks of the treated groups for about ten days. At the end of the observation, the chicks which survived the challenge were weighed.

Several tests at different pyrazole administration rates were conducted. Various numbers of chicks were placed in each treatment group in the different tests, which are summarized below. For each test, the survival rate, and the average weight of the surviving chicks in each treatment group are shown. One hundred gm./ton is equal to about 5 mg./kg./day.

| | Test A | |
|---|---|---|
| Compound | Survival | Avg. Wt. |
| 1-(2-hydroxyethyl)-3-nitro-4-pyrazolecarboxamide, 100 gm./ton | 20/36 | 94 gm. |
| Infected Controls | 24/72 | 85 gm. |
| | Test B | |
| Compound | Survival | Avg. Wt. |
| 1-allyl-3-nitro-4-pyrazolecarboxamide, 200 gm./ton | 26/36 | 88 gm. |
| 1-(2-hydroxyethyl)-3-nitro-4-pyrazolecarboxamide, 200 gm./ton | 35/36 | 107 gm. |
| Infected Controls | 15/36 | 78 gm. |
| | Test C | |
| Compound | Survival | Avg. Wt. |
| 2-(4-carbamoyl-3-nitro-pyrazol-1-yl)ethyl acetate, 200 gm./ton | 29/48 | 67 gm. |
| 1-(2-ethoxyethyl)-3-nitro-4-pyrazolecarboxamide, 200 gm./ton | 25/48 | 62 gm. |
| 1-allyl-3-nitro-4-pyrazolecarboxamide, 200 gm./ton | 25/48 | 64 gm. |
| 1-(2-hydroxyethyl)-3-nitro-4-pyrazolecarboxamide, 200 gm./ton | 34/48 | 71 gm. |
| Infected Controls | 6/48 | 56 gm. |

The severity of the challenges was different in each of the three tests, but all of the challenges were sufficiently severe to kill from 60 percent to almost 90 percent of the infected control chicks. In all instances, administration of the 3-nitropyrazole compound reduced the mortality in the treated chicks, and in some instances virtually all of the treated chicks survived the challenge.

Chronic respiratory disease, also known as avian mycoplasmosis, is a severe infection caused by *Mycoplasma gallisepticum*. The organism frequently infects embryonated eggs, where it kills the embryos or infects the chicks which hatch from the eggs. The disease is common in chickens and turkeys, and frequently occurs as outbreaks in flocks of 4- to 8-week-old birds.

EXAMPLE 34

Mycoplasma gallisepticum in chickens

A group of broiler type chickens, weighing about 1265 gm., were obtained from a homogeneous source flock. The birds were allocated into 12-bird treatment groups of equal weight. Four treatment groups were used in each of the treatments, including the untreated infected controls; two groups were held as normal controls.

The birds, other than the normal controls, were challenged by administering two 0.2 ml. injections of a freshly thawed *M. gallisepticum* culture to each bird, one injection in the wing vein and one in the air sac. Immediately after the challenge, four of the treatment groups were treated by injecting 25 mg./kg., intramuscularly, of 1-(2-hydroxyethyl)3-nitro-4-pyrazolecarboxamide to each chicken. The other four treated groups received the same compound at 2 gm./gal. (about 50 mg./kg./day) in their drinking water for a period of 4-½ days after the challenge was administered.

The birds were held and observed for about 3 weeks. Mortality in the experiment was negligible. At the end of the observation period, the birds were sacrificed and examined for *M. gallisepticum* lesions of the air sac. A sample of blood from each bird was tested to determined the presence of *M. gallisepticum* antibodies. Essentially all the challenged birds had antibody, indicating that the challenge organism had infected all the birds. The final average weights and the air sac lesion counts are shown below.

| Treatment | Air Sac Lesions | Avg. Wt. |
|---|---|---|
| 2.0 gm./gal. | 24/47 | 2188 gm. |
| 25 mg./kg. (injected) | 41/48 | 2093 gm. |
| Infected Controls | 44/48 | 1930 gm. |
| Normal Controls | 0/24 | 2247 gm. |

Since the challenge in this experiment was not severe enough to cause serious mortality of the infected birds, the effect of the infection is seen in air sac lesions and a decrease in the birds' weight. Administration of the pyrazole reduced the incidence of lesions and increased the birds' weight in one case by an average of more than 160 gm. each, and in the other treatment by almost 260 gm.

Infections of *Escherichia coli* in fowl are called colibacillosis and take at least two forms. *E. coli* occurs harmlessly in the digestive tract of nearly all species of animals, but it often becomes pathogenic when the fowl are weakened or infected by some other agent, and it can be a primary pathogen. Colibacillosis in poultry is evidenced by pericarditis, perihepatitis and air sacculitis. Colibacillosis weakens the birds, thereby aggravating the injuries of a primary infection, and *E. coli* as a primary infection can be the cause of death in itself.

EXAMPLE 35

Colibacillosis in chickens

A group of chickens about 5 weeks old was obtained from a homogeneous source flock. The birds were allocated into 10-bird treatment groups of approximately identical weights.

Each treatment group was caged apart from other treatment groups throughout the experiment.

The medicated treatment groups were offered medicated feed containing the compounds, at concentrations shown below, continuously throughout the experiment. All of the birds, including untreated controls, were challenged the day after the first administration of medicated feed with a single 0.5 ml. injection into the air sac of a $10^{-2}$ dilution of an avian *E. coli* culture.

The birds were observed for approximately one week, and birds which died were counted and examined for air sac lesions, pericarditis, and perihepatitis at necropsy. At the end of the observation period, the surviving birds were sacrificed and examined for lesions. Surviving birds were weighed at the end of the observation period.

| Compound | Mortality | E. coli Lesions | Avg. Wt. |
|---|---|---|---|
| 2-(4-carbamoyl-3-nitropyrazol-1-yl)-ethyl acetate, 300 gm./ton | 1/30 | 9/30 | 1139 gm. |
| 1-(2-hydroxyethyl)-3-nitro-4-pyrazole-carboxamide, 300 gm./ton | 0/30 | 11/30 | 1103 gm. |
| 1-(2-ethoxyethyl)-3-nitro-4-pyrazole-carboxamide, 300 gm./ton | 0/30 | 11/30 | 1136 gm. |
| 1-allyl-3-nitro-4-pyrazolecarboxamide, 300 gm./ton | 0/30 | 16/30 | 1090 gm. |
| Infected Controls | 2/30 | 30/30 | 979 gm. |

In another experiment, 1-(2-hydroxyethyl)-3-nitro-4-pyrazolecarboxamide was administered in the feed to approximately 7-week-old chickens. The test was conducted, except for the initial age of the chickens, as was the test above. The results are shown in the table below. Birds which died during the test were not examined for lesions

| Pyrazole Concentration | Mortality | E. coli Lesions |
|---|---|---|
| 100 gm./ton | 3/12 | 5/9 |
| 300 gm./ton | 0/12 | 4/12 |
| 600 gm./ton | 0/12 | 2/12 |
| 1000 gm./ton | 0/12 | 0/12 |
| Infected Controls | 5/12 | 5/7 |

A further test was conducted in which four of the nitropyrazoles were administered in feed at 100 and 200 gm./ton levels. In this experiment, the chickens were about 5 weeks of age when the test began. The test method was as described above.

| Compound | Mortality | E. coli Lesions | Avg. Wt. |
|---|---|---|---|
| 1-allyl-3-nitro-4-pyrazolecarboxamide, 100 gm./ton | 16/40 | 40/40 | 1112 gm. |
| 1-allyl-3-nitro-4-pyrazolecaboxamide, 200 gm./ton | 11/40 | 31/40 | 1266 gm. |
| 1-(2-hydroxyethyl)-3-nitro-4-pyrazole-carboxamide, 100 gm./ton | 6/40 | 37/40 | 1209 gm. |
| 1-(2-hydroxyethyl)-3-nitro-4-pyrazole-carboxamide, 200 gm./ton | 2/40 | 31/40 | 1353 gm. |
| 2-(4-carbamoyl-3-nitropyrazol-1-yl)-ethyl acetate, 100 gm./ton | 10/40 | 38/40 | 1219 gm. |
| 2-(4-carbamoyl-3-nitropyrazol-1-yl)-ethyl acetate, 200 gm./ton | 6/40 | 31/40 | 1308 gm. |
| 3-nitro-1-vinyl-4-pyrazolecaboxamide, 100 gm./ton | 5/40 | 23/40 | 1109 gm. |
| 3-nitro-1-vinyl-4-pyrazolecarboxamide, 200 gm./ton | 6/40 | 20/40 | 918 gm. |
| Infected Controls | 21/40 | 40/40 | 1121 gm. |
| Normal Controls | 1/40 | 1/40 | 1361 gm. |

An additional test was conducted in which 1-(2-hydroxyethyl)-3-nitro-4-pyrazolecarboxamide was administered at different feed concentrations to chickens which were challenged with a single air sac injection of 0.5 ml. of a $10^{-1}$ dilution of an avian *E. coli* strain culture. The initial weight of the chickens averaged 940 gm. The test was conducted in general in the same way the first *E. coli* test described above was conducted.

| Treatment | Mortality | E. coli Lesions | Avg. Wt. |
|---|---|---|---|
| 300 gm./ton | 0/18 | 5/18 | 1302 gm. |
| 200 gm./ton | 0/18 | 16/18 | 1250 gm. |
| 100 gm./ton | 0/18 | 17/18 | 1239 gm. |
| Infected Controls | 2/24 | 21/22 | 1085 gm. |

The tests reported above uniformly illustrate the effectiveness of our compounds in controlling *E. coli* infections of poultry. In each test without exception, administration of the pyrazoles to poultry substantially reduced the ill effects of the *E. coli* challenge.

One of the oldest known poultry diseases is fowl cholera, also known as avian pasteurellosis. The disease is dangerous to all species of poultry, and to many species of wild birds. It is the most injurious bacterial disease of turkeys. Although the disease tends to be more severe in warmer parts of the world, fowl cholera is endemic or sporadically epidemic in most countries. It is caused by *Pasteurella multocida,* which often infects flocks of poultry without a detectable route of transmission to the flock.

EXAMPLE 36

Pasteurellosis in chickens

Young chickens were obtained from a homogeneous flock, and were randomly allocated into treatment groups of eight birds each. Each treatment group was kept separate from the other groups throughout the experiment.

The tested compound, 1-(2-hydroxyethyl)-3-nitro-4-pyrazolecarboxamide, was administered to two of the treatment groups at a concentration of 100 gm. of the compound per ton of feed, or about 5 mg./kg./day.

The day after administration of the test compound was begun, all of the birds, including two 8-bird groups of untreated control birds, were challenged with a tryptose broth culture of an avian *P. multocida* strain, as an intravenous injection of 0.5 ml. of the culture. The birds were observed for about 10 days, and all birds which died were examined for lesions of the liver indicative of pasteurellosis. The livers were also cultured to isolate *P. multocida* if present. At the end of the test, all surviving birds were sacrificed and their livers were also examined and cultured.

The results of the test are presented below. The number of birds from which *P. multocida* was isolated and the mortality rate of the birds during the test are reported, for each group and as the totals of the two groups receiving each treatment.

| Treatment | Culture Isolation | Mortality Rate |
|---|---|---|
| 1-(2-hydroxyethyl)-3-nitro-4-pyrazole-carboxamide | 6/8 | 2/8 |
|  | 3/8 | 0/8 |
| Total | 9/16 | 2/16 |
| Untreated controls | 8/8 | 8/8 |
|  | 8/8 | 6/8 |
| Total | 16/16 | 14/16 |

The induced pasteurellosis infection killed almost 90 percent of the infected, untreated birds. Administration of the 3-nitropyrazole reduced the mortality to only about 12 percent. At the same time, the presence of isolable *P. multocida* in about half of the treated birds shows that the pasteurellosis challenge was effectively administered to the treated birds.

EXAMPLE 37

Pasteurellosis in turkeys

A test similar to the test described above was performed to assure that the compounds are effective in turkeys as well as in chickens. The same compound was used at the rate of 100 gm./ton, or about 5 mg./kg./day. The birds used were Small White turkey poults which were about eight weeks of age when the tests began. The birds were allocated into 5-bird treatment groups, and compound administration was again begun a day before administration of a *P. multocida* challenge. The turkeys were challenged with 0.5 ml. of a $10^{-4}$ dilution of an avian *P. multocida* broth culture, administered intratracheally.

The birds were observed for ten days after administration of the challenge, and samples of heart and liver tissue of each bird were cultured to isolate *P. multocida.*

The table below reports the results of the test in the manner explained in the example above.

| Treatment | Culture Isolation | Mortality Rate |
|---|---|---|
| 1-(2-hydroxyethyl)-3-nitro-4-pyrazole-carboxamide | 1/5 | 1/5 |
| Untreated Controls | 4/5 | 4/5 |

The challenge here was somewhat less virulent than the challenge in the chicken test reported above, but it was virulent enough to kill 80 percent of the untreated control turkeys. At the same time, the poults to which the compound was administered experienced only a 20 percent mortality rate.

Finally, two examples reporting typical tests of the compounds in swine will be presented.

EXAMPLE 38

Lymphadenitis in swine

The same 3-nitropyrazole tested in the example immediately above was also tested to determine its ability to prevent lymphadenitis, or jowl abscess, infections in swine. One group of 12 young swine was treated with the 3-nitropyrazole compound as a feed additive at the rate of 200 gm. per ton of feed, and another group of 12 swine was held as infected controls.

Administration of the 3-nitropyrazole began shortly before the administration of the challenge, and continued throughout the 7-week test.

All of the swine were challenged with a culture of group E streptococci isolated from jowl abscesses of an infected pig. The challenge organisms were administered as a dispersion in the swine's drinking water.

After 7 weeks, all of the swine were slaughtered, and their cervical areas were examined for the presence of the abscesses caused by lymphadenitis infections. No abscesses were found in any of the treated swine. Abscesses were found in 9 off the 12 infected control animals.

It is interesting to note that the compound is secreted in sow's milk. It is therefore possible that administration of the compound to a sow could also protect her nursing pigs from infections.

EXAMPLE 39

Growth promotion in swine

The same 3-nitropyrazole tested above was used in a growth promotion test in swine. The pigs weighed 25–30 lbs. when the test began, and were housed and fed according to good commercial practice for 28 days. The pigs in the treated group received feed containing 300 gm. per ton of the 3-nitrogpyrazole compound. The results of the test are shown below.

| Treatment | Averge Daily Gain | Average Daily Feed Consumption | Feed/Gain |
|---|---|---|---|
| Control | 0.90 lb. | 1.95 lbs. | 2.13 |
| 300 gm./ton | 1.01 lbs. | 2.00 lbs. | 1.96 |

The test reported above, each treatment group of which comprised four replications of six pigs each, shows very clearly that our 3-nitropyrazole compound allowed the treated pigs to grow more rapidly and efficiently than did the control pigs.

Methods of treating animals with certain of the compounds described above, making use of the antimicrobial, particularly antibacterial, and parasiticidal properties of the compounds, are an integral and important part of the invention.

One such embodiment of the invention is a method of preventing and treating blackhead disease, salmonellosis, colibacillosis, fowl cholera and chronic respiratory disease of poultry which comprises the administration to the poultry of a disease-preventative or curative amount of a compound of this invention of the formula

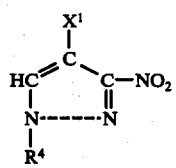

wherein $R^4$ represents
A. $C_2$-$C_4$ alkenyl,
B. cyclopropylmethyl,
C. oxopropyl,
D. $C_1$-$C_3$ alkyl,
E. benzyl,
F. $C_2$-$C_3$ alkyl substituted with
  1. hydroxy,
  2. chloro, or
  3. bromo, or
G. ethyl substituted with
  1. $C_1$-$C_2$ alkoxy,
  2. $C_1$-$C_2$ alkylsulfonyl, or

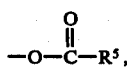   (3)

wherein $R^5$ represents
  a. $C_1$-$C_2$ alkyl,
  b. $C_1$-$C_2$ alkoxy,
  c. phenoxy,
  d. phenyl, or
  e. phenyl monosubstituted with
    1. methyl, or
    2. halo; and
$X^1$ represents
A. cyano, or

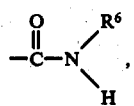   (B)

wherein $R^6$ represents
  1. hydrogen, or
  2. methyl.

The administration of the above compounds for the prevention and treatment of salmonellosis of poultry is a preferred method of our invention, because of the remarkable effectiveness of our method against salmonellosis. Accordingly, the above compounds constitute a preferred class of compounds of this invention.

Another embodiment of our invention is a method of preventing or treating pasteurella respiratory infections of cattle which comprises administering to the cattle a diseasepreventive or curative amount of a compound of this invention of the formula

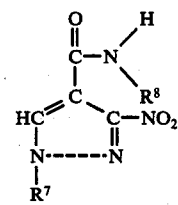

wherein $R^7$ represents
A. nonyl,
B. hydroxyethyl,
C. nitrophenyl,
D. nitrothiazolyl, or

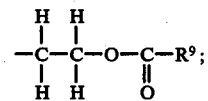   (E)

$R^8$ represents
A. hydrogen, or
B. methyl;
$R^9$ represents
A. amino, or
B. methyl.

The above compounds constitute another preferred class of compounds of this invention.

The compound which is preferred in both methods is 1-(2-hydroxyethyl)-3-nitro-4-pyrazolecarboxamide.

The compounds can be used both to prevent and to treat the named diseases. It is most efficient to begin preventive administration at a time when a disease outbreak is to be expected, such as when the poultry or cattle are under undue stress, as from inclement weather or shipment of cattle. However, there is no reason not to administer the compound preventively throughout life.

Curative administration should be started as soon as signs of disease appear in the herd or poultry flock. Reference to the examples will show that treatment, as well as prevention, of disease is often effective when only a single dose of the compound is administered.

The amount of the compound which should be administered depends on a number of factors. Higher rates are usually used for the cure of existing infection, and lower rates are usually adequate for disease prevention. More severe infection, or the risk of more severe infection, calls for higher administration rates. Thus, the highest administration rates are usually used for the treatment of a severe disease outbreak, and the lowest rates for prevention when there is only a mild risk of infection.

The optimum rate must be determined individually in each case. For poultry, the usual dosage range is from about 1 mg./kg./day to about 100 mg./kg./day. For cattle, it is from about 1 mg./kg./day to about 50 mg./kg./day. It will usually be found that the optimum rate is in the preferred ranges from about 5 mg./kg./day to about 50 mg./kg./day for poultry, and from about 2 mg./kg./day to about 35 mg./kg./day for cattle. Those skilled in veterinary medicine will recognize that it will sometimes be necessary to administer doses outside the stated range.

The compounds are administered in the manners usual in veterinary medicine, which will be discussed briefly. Oral administration of the compounds is preferred.

Whether a disease-preventive or a curative administration of a 3-nitropyrazole is desired, the usual objective is to administer a regular daily dose of the compound. Such continuous administration is most easily accomplished by mixing the compound in the feed or drinking water, but percutaneous methods are also effective and convenient.

The administration of the 3-nitropyrazoles to animals to be tested or protected is carried out through the use of the antibacterial compositions described below. Many types of antibacterial compositions may be used, depending upon the convenience of administration. All types of compositions are effective if porperly used according to the usual veterinary pharmaceutical teachings. In general, the compositions are prepared according to the usual methods, and are novel only because of the presence therein of our 3-nitropyrazoles.

Percutaneously-administered antibacterial compositions include injectable solutions and suspensions, and depot formulations including matrices and implants. Orally-administered compositions include drenches, capsules, tablets and the like, drinking water and medicated feeds. Such compositions are described in detail below.

The amounts or concentrations of the 3-nitropyrazoles in our antibacterial compositions are irrelevant to the efficacy of the compounds. Obviously, the dosage administered an animal depends upon the concentration of the compound in a composition and the amount of the composition administered. It is therefore impossible to specifiy amounts or concentrations of compounds in the compositions which will make the compositions efficacious, no matter how much of the compositions may be administered. The amounts of compounds to be contained in a composition are therefore described here as "antibacterially-effective", recognizing that one of ordinary skill in the veterinary pharmaceutical art can easily compute the amount of any composition to administer in order to provide a proper dosage, making use of the dosage rate description provided above.

In general, all of the antibacterial compositions may be described as comprising an antibacterially-effective amount of a compound of this invention and a physiologically-acceptable inert carrier.

It is usual to prepare a percutaneous dosage form of a pharmaceutical compound by dissolving or suspending the compound in a physiologically-acceptable formulation. For example, the compound may be dissolved in a physiologically-acceptable inert carrier such as water, or polyethylene or polypropylene glycol. The compound may also be finely powdered and suspended in a water-based formulation, where water is the inert carrier, or in a liquid inert carrier such as a vegetable oil or a glycol. Suitable adjuvants are necessary to keep the pyrazole suspended. The adjuvants can be chosen from among the viscosity-increasing agents, such as carboxymethylcellulose, polyvinylpyrrolidone, gelatin, and the alginates. Surfactants, such as, for example, lecithin, alkylphenol polyethylene oxide adducts, naphthalenesulfonates, alkylbenzenesulfonates, and the polyoxyethylene sorbitan esters are also useful for suspending the 3-nitropyrazoles in liquids. In addition, other substances which affect the hydrophilicity, density, and surface tension of the liquid can help in making injectable suspensions. For example, silicone antifoams, glycols, sorbitol, and sugars can be useful suspending agents in individual cases.

It is possible to extend the interval between percutaneous doses by formulating a compound in a form which delays or sustains entry into the system. Sustained action of the compound can be obtained by formulating it in an inert carrier matrix which physically inhibits dissolution of the compound into the body fluids. The matrix is administered to the bird or animal by injection into a part of the body where it remains as a depot from which the pyrazole slowly dissolves.

Matrix formulations are now well known in the pharmaceutical art. They are regularly formulated in waxy semi-solids such as vegetable waxes and high-molecular-weight polyethylene glycols.

Another way to delay or sustain absorption of a pyrazole is to encapsulate it in an implant. Such implants comprise a pellet or capsule made of an inert carrier which is a physiologically-acceptable permeable polymer such as silicone rubber or silicone-containing plastics. Other polymers are also known in the art. The pyrazole may be enclosed in a membrane of the polymer, or may be dispersed throughout a solid polymeric implant. In either case, the implant is surgically implanted, preferably in a part which is removed from the carcass after slaughter. The body fluids slowly leach the pyrazole from the implant. Such implants can be designed to delay the availability of the pyrazole for any reasonable length of time. Variations in the formulation of the polymer which forms the implant, the concentration of the pyrazole in the implant, and in the thickness of the polymeric wall, are used to control the length of time over which the pyrazole becomes available.

It is also possible to administer the 3-nitropyrazole to cattle or other animals in such oral pharmaceutical dosage forms as drenches, capsules, tablets, and the like. Such dosage forms have an obvious disadvantage of difficulty of administration to the animal, but may be administered when the animal is so ill that it is not eating or drinking.

The 3-nitropyrazole can be tabletted by the standard methods. The compound is compatible with the normal excipients and lubricants, used as inert carriers, and the heating incident to compression of a tablet does not damage the compound. Of course, the compound can also be filled into capsules as inert carriers if it is desired to do so; the filling of capsules is a simple mechanical operation which has no effect on the compound.

When a pyrazole is to be administered in drench form, the practitioner need only compute the proper amount of the pyrazole, dissolve or suspend it in an appropriate amount of water as inert carrier, and administer the drench in the usual manner. The solvents and suspending agents discussed above as ingredients of injectable formulations are also useful in formulating drenches. The compound may be conveniently supplied as a dry mixture of the finely powdered pyrazole with suspending agents as inert carriers, as a drench mixture ready to administer, or as a concentrated solution or suspension to be diluted with water and mixed before administration.

The pyrazole may be administered using drinking water as inert carrier. The farmer need only add a concentration of a pyrazole to the water sufficient to supply each animal's or bird's daily dose in the amount of water which the creature consumes daily. The medicated water is most easily prepared by first preparing a concentrated solution or suspension, or a powdered mixture of the compound with suspending agents as inert carriers, such as were described under drench formulations.

The best method of administering the compounds is in the feed. The animal feeds, to be used as inert carriers, in which the nitropyrazoles are mixed may be any feed suitable for the nutrition of cattle, poultry, or other animals to be treated. A cattle feed may be either a solid feed suitable for cattle which have a developed rumen function, or may be a milk replacer adapted to the nutrition of unweaned calves.

The solid feed compositions should contain a concentration of the 3-nitropyrazole which provides, to a bird or animal consuming its daily requirement of the feed composition, a daily dose of a pyrazole within the scope of our disease-preventing and curative method. The concentration varies with the animal's weight, the amount of food it consumes daily, and the dose of pyrazole which it is desired to administer.

It is usual to make a concentrated feed premix as a raw material for medicated feeds. The formulation of the premix is guided slowly by convenience in making feed from the premix and by economy; they usually comprise from about 10 to about 400 gm. of the pyrazole compound per pound, and an inert liquid or solid premix carrier.

Liquid inert carriers suitable for premix use include glycols such as polyethylene glycols and propylene glycol, inert oils including vegetable oils and refined mineral oils, and physiologically-acceptable solvents such as water and ethanol. Solid inert premix carriers include vermiculite, diatomaceous earth, physiologically-acceptable clays such as attapulgite and montmorillonite, and granulated or powdered feed components such as cracked corn, soybean meal, alfalfa meal, rice hulls, corncobs, cracked wheat or oats, and waste materials of grain processing.

All of the methods of formulating, mixing, and pelleting feeds normally used in the feed art are entirely appropriate for manufacturing feed compositions containing the pyrazole of our methods.

Calves which are too young to wean, but which have been removed from their dams, are fed on artificial milk preparations known as milk replacers. The preparations are aqueous suspensions, or emulsions, of nutritive ingredients. The 3-nitropyrazole is readily mixed with milk replacers. While the daily dose of the compound is relatively constant, the amount of milk replacer which the calves are fed varies widely. the concentration of the compound in the feed composition should be sufficient that a calf, consuming the composition, ingests eacy day the proper dose of the compound.

We claim:
1. An antibacterial composition which comprises a physiologically-acceptable inert carrier and an antibacterially-effective amount of a compound of the formula

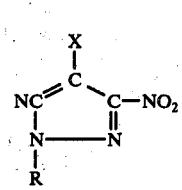

wherein R represents

A. $C_3-C_4$ epoxyalkyl,
B. hydrogen,
C. $C_1-C_{10}$ alkyl, $C_2-C_{10}$ alkenyl, $C_3-C_{10}$ alkynyl, $C_3-C_{10}$ cycloalkyl, cyclopropylmethyl, $C_3-C_{10}$ cycloalkenyl, $C_2-C_{10}$ alkyl mono- or disubstituted with halo or $C_1-C_3$ alkoxy, or $C_1-C_{10}$ alkyl monosubstituted with
  1. mercapto,
  2. carboxamido,
  3. keto oxygen,
  4. hydroxy,
  5. phthalimido,
  6. $C_1-C_3$ alkylthio,
  7. $C_1-C_3$ alkylsulfonyl,
  8. $C_1-C_3$ alkanoyl,
  9. phenyl,
  10. phenyl monosubstituted with
    a. $C_1-C_3$ alkyl,
    b. $C_1-C_3$ haloalkyl,
    c. hydroxy, or
    d. halo,

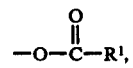 (11)

wherein $R^1$ represents
  a. $C_1-C_3$ alkyl,
  b. $C_1-C_3$ alkoxy,
  c. $C_1-C_3$ haloalkyl,
  d. amino,
  e. $C_3-C_6$ cycloalkyl,
  f. phenoxy,
  g. phenyl, or
  h. phenyl monosubstituted with
    1. $C_1-C_3$ alkyl,
    2. $C_1-C_3$ haloalkyl,
    3. halo, or
    4. hydroxy, or
  12. cyano, or
D. 4-nitrophenyl, 5-nitro-2-thiazolyl, or 3-nitro-2-pyridyl; and
X represents
A. 5-methylamino-1,3,4-thiadiazol-2-yl,
B. cyano,

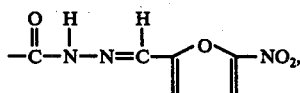 (C)

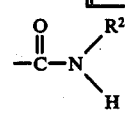 (D)

wherein $R^2$ represents
  1. hydrogen, or
  2. $C_1-C_6$ alkyl; or

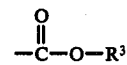 (E)

wherein $R^3$ represents
$C_1-C_6$ alkyl;
provided that a $C_1$ alkyl R group is substituted only with phenyl or substituted phenyl.

2. A composition of claim 1 wherein the compound is of the formula

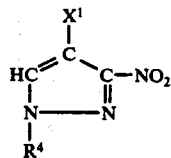

wherein R⁴ represents
A. C₂–C₄ alkenyl,
B. cyclopropylmethyl,
C. oxopropyl,
D. C₁–C₃ alkyl,
E. benzyl,
F. C₂–C₃ alkyl substituted with
  1. hydroxy,
  2. chloro, or
  3. bromo, or
G. ethyl substituted with
  1. C₁–C₂ alkoxy,
  2. C₁–C₂ alkylsulfonyl, or (3) 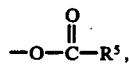

wherein R⁵ represents
  a. C₁–C₂ alkyl,
  b. C₁–C₂ alkoxy,
  c. phenoxy,
  d. phenyl, or
  e. phenyl monosubstituted with
    3. methyl, or
    2. halo; and
X¹ represents
A. cyano, or

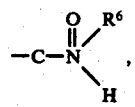

wherein R⁶ represents
  1. hydrogen, or
  2. methyl.

3. A composition of claim 1 wherein the compound is of the formula

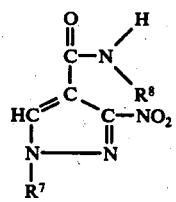

wherein R⁷ represents
A. nonyl,
B. hydroxyethyl,
C. 4-nitrophenyl,
D. nitrothiazolyl, or

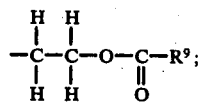

R⁸ represents
A. hydrogen, or
B. methyl;
R⁹ represents
A. amino, or
B. methyl.

4. A composition of claim 1 wherein R represents hydrogen, alkyl, alkenyl, alkynyl, cyclopropylmethyl, cycloalkyl, cycloalkenyl, alkyl mono- or disubstituted with halo or alkoxy, or alkyl monosubstituted with mercapto, carboxamido, keto oxygen, hydroxy, phthalimido, alkylthio, alkylsulfonyl, alkanoyl, phenyl, substituted phenyl, cyano or

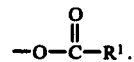

5. A composition of claim 4 wherein R represents hydrogen, alkyl, alkenyl, alkynyl, cyclopropylmethyl, cycloalkyl, cycloalkenyl, alkyl mono- or disubstituted with halo or alkoxy, or alkyl monosubstituted with mercapto, carboxamido, keto oxygen, hydroxy, alkylthio, alkylsulfonyl, alkanoyl, phenyl, substituted phenyl or cyano.

6. A composition of claim 5 wherein R represents hydrogen, alkyl, alkenyl, cyclopropylmethyl, alkyl mono- or disubstituted with halo or alkoxy, or alkyl monosubstituted with hydroxy or alkylsulfonyl.

7. A composition of claim 6 wherein R represents hydrogen, C₁–C₄ alkyl, C₂–C₃ alkenyl, cyclopropylmethyl, C₂–C₄ alkyl mono- or disubstituted with halo or alkoxy, or C₂–C₄ alkyl monosubstituted with hydroxy or alkylsulfonyl.

8. A composition of claim 4 wherein X represents cyano, (B) 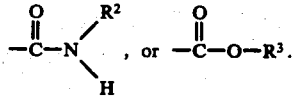

9. A composition of claim 5 wherein X represents cyano,

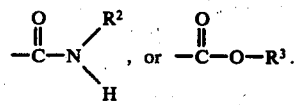

10. A composition of claim 6 wherein X represents cyano,

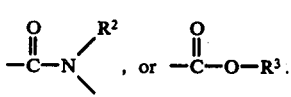

11. A composition of claim 7 wherein X represents cyano, (E) 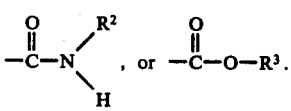

12. A composition of claim 11 wherein X represents cyano or

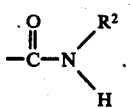

13. The composition of claim 12 wherein the compound is 1-(2-hydroxyethyl)-3-nitro-4-pyrazolecarboxamide.

14. The composition of claim 12 wherein the compound is 1-(2-hydroxyethyl)-N-methyl-3-nitro-4-pyrazolecarboxamide.

15. The composition of claim 12 wherein the compound is 1-(2-ethoxyethyl)-3-nitro-4-pyrazolecarboxamide.

16. The composition of claim 12 wherein the compound is 1-allyl-3-nitro-4-pyrazolecarboxamide.

17. The composition of claim 12 wherein the compound is 3-nitro-1-vinyl-4-pyrazolecarboxamide.

18. The composition of claim 12 wherein the compound is 1-(2-hydroxypropyl)-3-nitro-4-pyrazolecarboxamide.

19. The composition of claim 12 wherein the compound is 1-(3-chloropropyl)-3-nitro-4-pyrazolecarbonitrile.

20. The composition of claim 12 wherein the compound is 1-(2-ethylsulfonylethyl)-3-nitro-4-pyrazolecarboxamide.

21. The composition of claim 12 wherein the compound is 1-cyclopropylmethyl-3-nitro-4-pyrazolecarboxamide.

22. The composition of claim 12 wherein the compound is 1-(2-chloroethyl)-3-nitro-4-pyrazolecarbonitrile.

23. A composition of claim 4 wherein R represents alkyl monosubstituted with

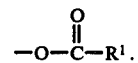

24. A composition of claim 23 wherein X represents cyano,

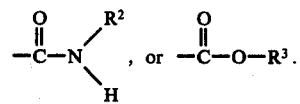

25. A composition of claim 24 wherein X represents cyano or

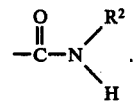

26. The composition of claim 25 wherein the compound is 2-(4-carbamoyl-3-nitropyrazol-1-yl)ethyl acetate.

27. The composition of claim 25 wherein the compound is [2-(4-carbamoyl-3-nitropyrazol-1-yl)ethyl] phenyl carbonate.

28. A composition of claim 7 wherein X represents thiadiazolyl or substituted thiadiazolyl.

29. The composition of claim 28 wherein the compound is 2-amino-5-(1-methyl-3-nitro-4-pyrazolyl)-1,3,4-thiadiazole.

30. An antibacterial composition which comprises a physiologically-acceptable inert carrier and an antibacterially-effective amount of 1,1'-(2,5-cyclohexadien-1,4-ylene)-bis-(3-nitro-4-pyrazolecarboxamide).

* * * * *

UNITED STATES PATENT OFFICE
CERTIFICATE OF CORRECTION

Patent No. 4,066,776      Dated January 3, 1978

Inventor(s) Reuben G. Jones and Norman H. Terando

It is certified that error appears in the above-identified patent and that said Letters Patent are hereby corrected as shown below:

Column 2, line 23:    "Vatre" should read --Vatne--.

Column 8, line 26:    "have" should read --here--.

Column 9, line 42:    "notro" should read --nitro--.

Column 14, line 56:    "lyl)" should read -- 1-yl) --.

Column 17, line 60:    "hydroxyethyl)-b 3" should read --hydroxyethyl)-3--.

Column 18, line 21:    "provided" should read -- proved --.

Column 18, line 52:    "out" should read --our--.

Column 20, line 2:    "pyrazolecarboxamie" should read --pyrazolecarboxamide--.

Column 24, line 32:    "shown" should read --show--.

Column 24, line 48:    "rates" should read --rated--.

Column 27, line 31:    "diplococuss" should read --diplococcus--.

Column 27, line 50:    "temperature" should read --temperatures--

Column 28, line 62:    "extrememly" should read --extremely--.

Column 34, line 11:    "nitrogpyrazoles" should read --nitropyrazoles--.

UNITED STATES PATENT OFFICE
CERTIFICATE OF CORRECTION

Patent No. 4,066,776　　　　　　　　　　Dated January 3, 1978

Inventor(s) Reuben G. Jones and Norman H. Terando

It is certified that error appears in the above-identified patent and that said Letters Patent are hereby corrected as shown below:

Column 36, line 56: "nitrogpyrazole" should read --nitropyrazole--.

Column 39, line 17: "porperly" should read --properly--.

Signed and Sealed this

Fifteenth Day of May 1979

[SEAL]

Attest:

RUTH C. MASON
Attesting Officer

DONALD W. BANNER
Commissioner of Patents and Trademarks